US012779141B2

(12) United States Patent
Bradenham, Jr.

(10) Patent No.: US 12,779,141 B2
(45) Date of Patent: Nov. 3, 2026

(54) SYSTEM, APPARATUS, AND METHOD FOR PROVIDING PERIPHERAL INTRAVENOUS ACCESS

(71) Applicant: Ben Persons Bradenham, Jr., Richmond, VA (US)

(72) Inventor: Ben Persons Bradenham, Jr., Richmond, VA (US)

(*) Notice: Subject to any disclaimer, the term of this patent is extended or adjusted under 35 U.S.C. 154(b) by 72 days.

(21) Appl. No.: 18/823,226

(22) Filed: Sep. 3, 2024

(65) Prior Publication Data

US 2025/0152856 A1 May 15, 2025

Related U.S. Application Data

(60) Provisional application No. 63/598,082, filed on Nov. 11, 2023.

(51) Int. Cl.
*A61M 5/52* (2006.01)

(52) U.S. Cl.
CPC ....... *A61M 5/52* (2013.01); *A61M 2205/0216* (2013.01); *A61M 2205/025* (2013.01); *A61M 2210/083* (2013.01)

(58) Field of Classification Search
CPC .... A61F 5/3753; A61F 5/0118; A61F 5/3723; A61F 5/3738; A61F 5/373; A61F 5/3761; A61F 5/05858; A61F 5/05866; A61M 5/52; A61M 25/02
See application file for complete search history.

(56) References Cited

U.S. PATENT DOCUMENTS

| | | | | |
|---|---|---|---|---|
| 4,123,052 A * | 10/1978 | Perkins | .............. | A63B 21/4017 446/26 |
| 4,884,561 A * | 12/1989 | Letson, Sr. | ........... | A61F 5/0125 2/24 |
| 5,662,594 A * | 9/1997 | Rosenblatt | .............. | A61F 5/013 2/2.5 |
| 6,569,067 B1 * | 5/2003 | Madole | .............. | A63B 23/1245 482/148 |

(Continued)

FOREIGN PATENT DOCUMENTS

| | | | |
|---|---|---|---|
| CA | 3013903 A1 * | 2/2019 | ............ A61M 25/02 |
| KR | 20200089023 A * | 7/2020 | ............ A61F 5/042 |

OTHER PUBLICATIONS

Webpage advertisement for IV Arm/Elbow Board printed on Aug. 12, 2024 from https://www.sedationkit.com/product/iv-arm-elbow-board-adult/ (6 pages).

(Continued)

*Primary Examiner* — Ophelia A Hawthorne
(74) *Attorney, Agent, or Firm* — Keefe IP Law, PLLC

(57) ABSTRACT

An apparatus for stabilizing a limb against flexion around a joint of the limb is disclosed. The apparatus has a joint member having an intermediate portion disposed between a first end portion and a second end portion of the joint member, a first movable member removably attachable to the first end portion, and a second movable member removably attachable to the second end portion. The intermediate portion is configured to receive the joint. The second end portion is angled from the first end portion at a joint angle that is opposite to a flexion direction of the limb about the joint.

20 Claims, 16 Drawing Sheets

(56) References Cited

U.S. PATENT DOCUMENTS

| | | | |
|---|---|---|---|
| 2017/0049996 | A1 | 2/2017 | Klinkner |
| 2019/0201258 | A1 | 7/2019 | Di Lauro |

OTHER PUBLICATIONS

Webpage advertisement for Arm-Elbow Board printed on Aug. 12, 2024 from https://www.fix-iv.com/en/products/ (1 page).

Webpage advertisement for Arm-Elbow Board printed on Aug. 12, 2024 from https://www.ivhouse.com/products/tlc-elbow-splint (2 pages).

Webpage advertisement for pediatric "No No" Device printed on Aug. 12, 2024 from https://www.nono-armhelper.com/shop (11 pages).

Webpage advertisement for surgical positioning device printed on Aug. 12, 2024 from https://www.alimed.com/alimed-armboard-pads.html?pid=83312&gclid=EAlalQobChMI9_3gqors_gIV8e3jBx28YQO-EAQYAyABEgLuwfD_BWE (2 pages).

Webpage advertisement for c. Veterinary IV stabilizers printed on Aug. 12, 2024 from https://www.pennvet.com/customer/portal/catalog/home/productfamilydetail/ss0127/iv+stabilizers (1 page).

Webpage advertisement for static elbow splint printed on Aug. 12, 2024 from https://www.amazon.com/LANREN-Shipping-Hemiplegic-Rehabilitation-Training/dp/B091KVGKN2?th=1 (4 pages).

Webpage advertisement for ii. 3 point pressure elbow extension splint printed on Aug. 12, 2024 from https://www.facebook.com/langhandtherapy/photos/a.1725759940889140/1998367720295026/?type=3 (1 page).

Webpage advertisement for dynamic range of motion splint printed on Aug. 12, 2024 from https://www.performancehealth.com/derom-dynamic-range-of-motion-splint (3 pages).

Webpage advertisement for air cast printed on Aug. 12, 2024 from https://www.medicalexpo.com/prod/aircast/product-96041-599465.html (3 pages).

Moureau, N. L. et al. Vessel Health and Preservation: The Right Approach for Vascular Access. (Springer, 2019).

* cited by examiner

SYSTEM, APPARATUS, AND METHOD FOR PROVIDING PERIPHERAL INTRAVENOUS ACCESS

CROSS-REFERENCE TO RELATED APPLICATIONS

This application claims priority to U.S. provisional patent application No. 63/598,082 filed Nov. 11, 2023, the entire disclosure of which is incorporated herein by reference.

TECHNICAL FIELD

The present disclosure generally relates to a system, apparatus, and method for providing intravenous access, and more particularly to a system, apparatus, and method for providing peripheral intravenous access.

BACKGROUND

Peripheral intravenous (PIV) access is a common element of both inpatient and outpatient medical services. One characteristic of an aging population is the tendency for peripheral veins to become more difficult to safely cannulate, limiting the number of vessels that can be suitably used to deliver medications, intravenous fluid, or blood products. There are other forms of intravenous (IV) access when peripheral venous access cannot be obtained. “Mid-lines” and central venous forms of IV access such as Peripherally Inserted Central venous Catheters ‘PICCs’ or traditional central venous catheters can play an effective role when difficulty obtaining a PIV is encountered. However, the risks of catheter related thrombosis and infection in such situations can be significant and are higher with central venous access than in peripheral venous access.

The antecubital fossa (AC fossa) is one of the most cannulated sites for routine phlebotomy. The vessels are superficial, void of nearby nerves, and large enough to readily tolerate puncture without injury. Unfortunately, this site is not desirable for establishing and maintaining peripheral venous access using conventional techniques. This is because for an IV in the AC fossa to function, the patient’s arm is to stay in a nearly fully extended position. The angle of even a modestly flexed elbow is enough to displace or kink the thin catheter of a peripheral IV in the antecubital fossa, routinely rendering the PIV non-functional. For procedures in which sedation is used, a PIV in the AC fossa can present a particular challenge when patients emerge from deeper states of sedation into lighter states in which flexion at the elbow is a common reflexive movement. As noted above, flexion at the elbow commonly displaces or transiently kinks and occludes the IV, making it difficult to regain the ideal level of sedation. A dedicated caregiver is commonly tasked to extend the extremity, hopefully restoring flow through the IV into the vein or to replace the PIV entirely.

In emergency departments, larger gauge peripheral IVs are routinely desirable to quickly rehydrate, transfuse blood products, or deliver medications that are caustic to smaller vessels. For contrast enhanced imaging such as computed tomography (CT) or magnetic resonance imaging (MRI), effective IV access is to be robust enough to allow for a bolus of contrast to be infused, often in a rapid but controlled manner, with images taken in a specific timed sequence designed to evaluate patients for specific problems. Due to the ease in which AC vessels can be accessed, it is a site often used in the short term in the case of an alert, cooperative adult. However, despite how readily it can be cannulated, for the reasons described above this is not a site that can be effectively used for long given how easily it can become compromised.

Accordingly, a need in the art exists for maintaining effective peripheral intravenous access (PIV) in the AC fossa.

The exemplary disclosed system, apparatus, and method of the present disclosure are directed to overcoming one or more of the shortcomings set forth above and/or other deficiencies in existing technology.

SUMMARY OF THE DISCLOSURE

In one exemplary aspect, the present disclosure is directed to an apparatus for stabilizing a limb against flexion around a joint of the limb. The apparatus includes a joint member having an intermediate portion disposed between a first end portion and a second end portion of the joint member, a first movable member removably attachable to the first end portion, and a second movable member removably attachable to the second end portion. The intermediate portion is configured to receive the joint. The second end portion is angled from the first end portion at a joint angle that is opposite to a flexion direction of the limb about the joint.

In another aspect, the present disclosure is directed to a method. The method includes receiving a joint of a limb in an intermediate portion of a joint member, the intermediate portion disposed between a first end portion and a second end portion of the joint member, and the second end portion being angled from the first end portion at a joint angle, positioning the joint member so that the joint angle is opposite to a flexion direction of the limb about the joint, and removably attaching a first movable member, which has a first tapered portion, to the first end portion. The method also includes removably attaching a second movable member, which has a second tapered portion, to the second end portion, and forming an aperture at the joint with the first tapered portion and the second tapered portion so that the joint is visible through the aperture.

DETAILED DESCRIPTION AND INDUSTRIAL APPLICABILITY

Figure 1:
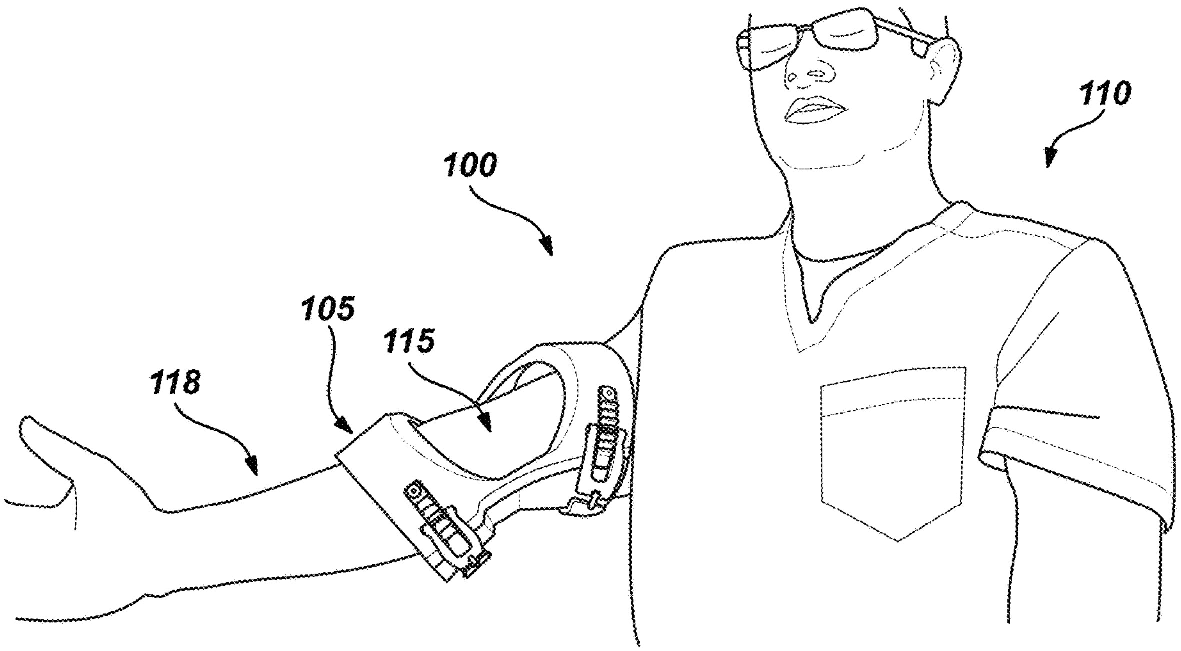
FIG. 1 is a side perspective view of an exemplary embodiment of the present invention.
Figure 2:
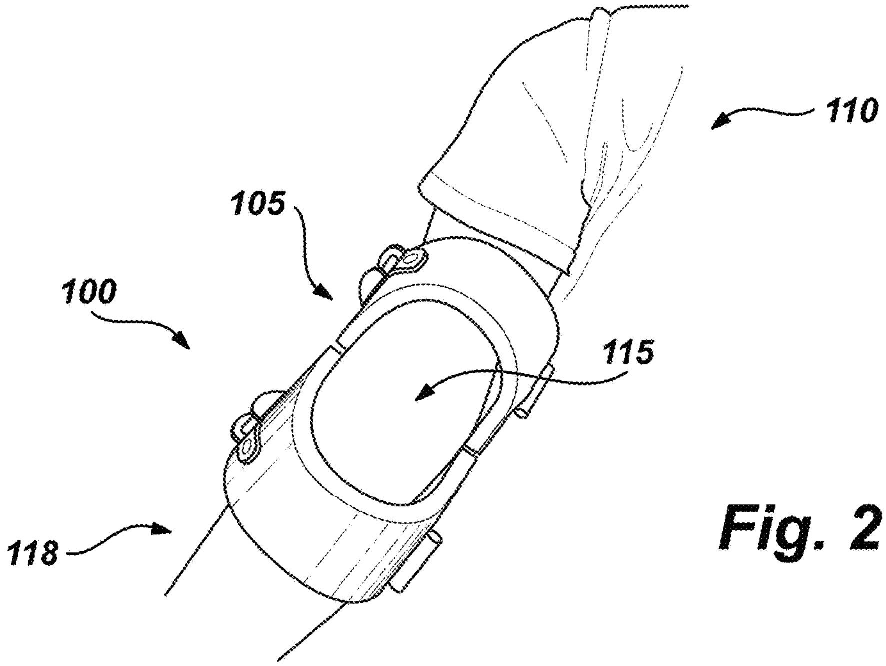
FIG. 2 is a top side perspective view of the exemplary embodiment of the present invention illustrated in FIG. 1.

The exemplary disclosed system, apparatus, and method may provide for stabilization of an arm (e.g., or a leg or other hinged joint) of a patient. FIGS. 1 and 2 illustrate an exemplary embodiment of the exemplary disclosed system, apparatus, and method. System 100 may include an apparatus 105 that may be utilized to stabilize a limb 118 such as an arm (e.g., or a leg or other hinged joint) of a patient 110 (e.g., against flexion at a joint). In at least some exemplary embodiments, the stabilization provided by system 100 may be used to facilitate stabilization and/or placement of a peripheral IV in an AC fossa 115 of patient 110 for any procedure involving sedation, contrast enhanced imaging study, intravenous therapy, prolonged phlebotomy, and/or any other suitable procedure. One or more users such as medical personnel (e.g., doctors, nurses, EMT personnel, medics, and/or any other suitable personnel) may assist with the fastening (e.g., donning) and removal of apparatus 105.

Figure 3:
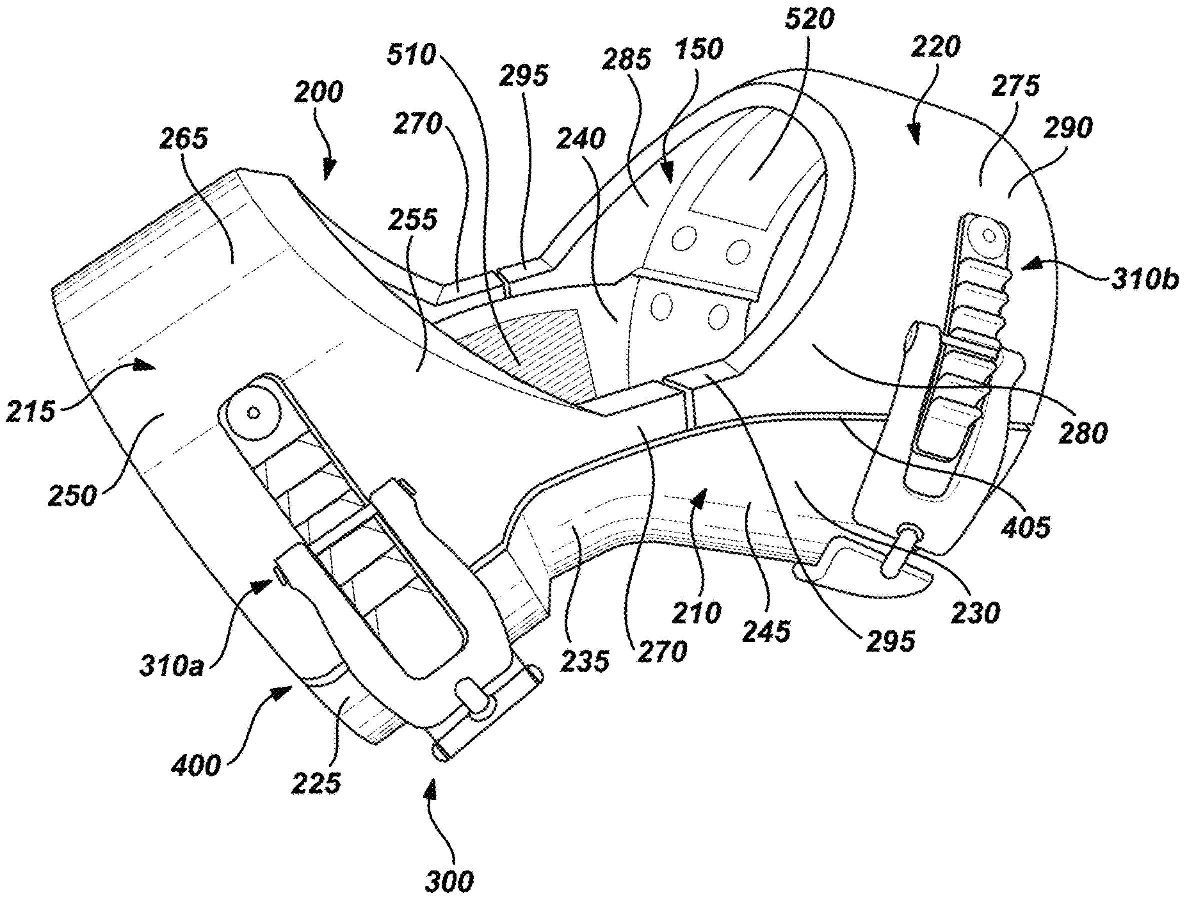
FIG. 3 is a right side, perspective view of the exemplary embodiment of the present invention illustrated in FIG. 1.

As illustrated in FIGS. 3-9, apparatus 105 may include a structural assembly 200, a fastening assembly 300, a sealing assembly 400, and an exemplary disclosed padding assembly. As illustrated in FIG. 3, structural assembly 200 may structurally support fastening assembly 300, sealing assembly 400, and the exemplary disclosed padding assembly.

Structural assembly 200 may include a joint member 210, a first movable member 215, and a second movable member 220. First movable member 215 and second movable member 220 may be movably attached (e.g., rotatably attached) to joint member 210.

Structural assembly 200 (e.g., joint member 210, first movable member 215, and second movable member 220) may be formed from any suitable structural material. For example, structural assembly 200 may be formed from structural plastic, metal, composite material, wood, fabric, ceramic, and/or any other suitable structural material. In at least some exemplary embodiments, structural assembly 200 may be formed from one or more thermoplastic polymeric materials. Structural assembly 200 may be formed from polyvinyl chloride (PVC) material, acrylonitrile butadiene styrene (ABS) material, polycarbonate material, PPS material, Polypropylene, HDPE, and/or any other suitable structural material. In at least some exemplary embodiments, structural assembly 200 may be formed from PVC or ABS material such as PVC or ABS hollow members (e.g., PVC or ABS pipe).

Joint member 210 may be any suitable member for movably supporting (e.g., rotatably supporting) first movable member 215 and second movable member 220, and for supporting and/or stabilizing a joint such as an elbow or knee of patient 110. Joint member 210 may serve as an arm cradle for an arm of patient 110 (e.g., or as a leg cradle for a leg of patient 110, or cradle for another hinged joint). Joint member 210 may include a first end portion 225, a second end portion 230, and an intermediate portion 235 disposed between first end portion 225 and second end portion 230. Intermediate portion 235 may be integrally formed with first end portion 225 and/or second end portion 230, and/or attached to first end portion 225 and/or second end portion 230 via any suitable technique such as mechanical fasteners (e.g., screws and/or bolts), welding, adhesive, snap-fit attachment, press-fit attachment, and/or any other suitable attachment technique. First end portion 225, second end portion 230, and intermediate portion 235 may form an interior surface 240 at an interior of joint member 210 that may face a joint such as an arm (e.g., an elbow) or a knee of patient 110 when patient 110 is wearing apparatus 105. First end portion 225, second end portion 230, and intermediate portion 235 may also form an exterior surface 245 at an exterior of joint member 210 that may face away from an arm (e.g., an elbow) or a leg (e.g., or other hinged joint) of patient 110 when patient 110 is wearing apparatus 105. Interior surface 240 and exterior surface 245 may thereby be formed on opposite sides of joint member 210 from each other.

Figure 4:
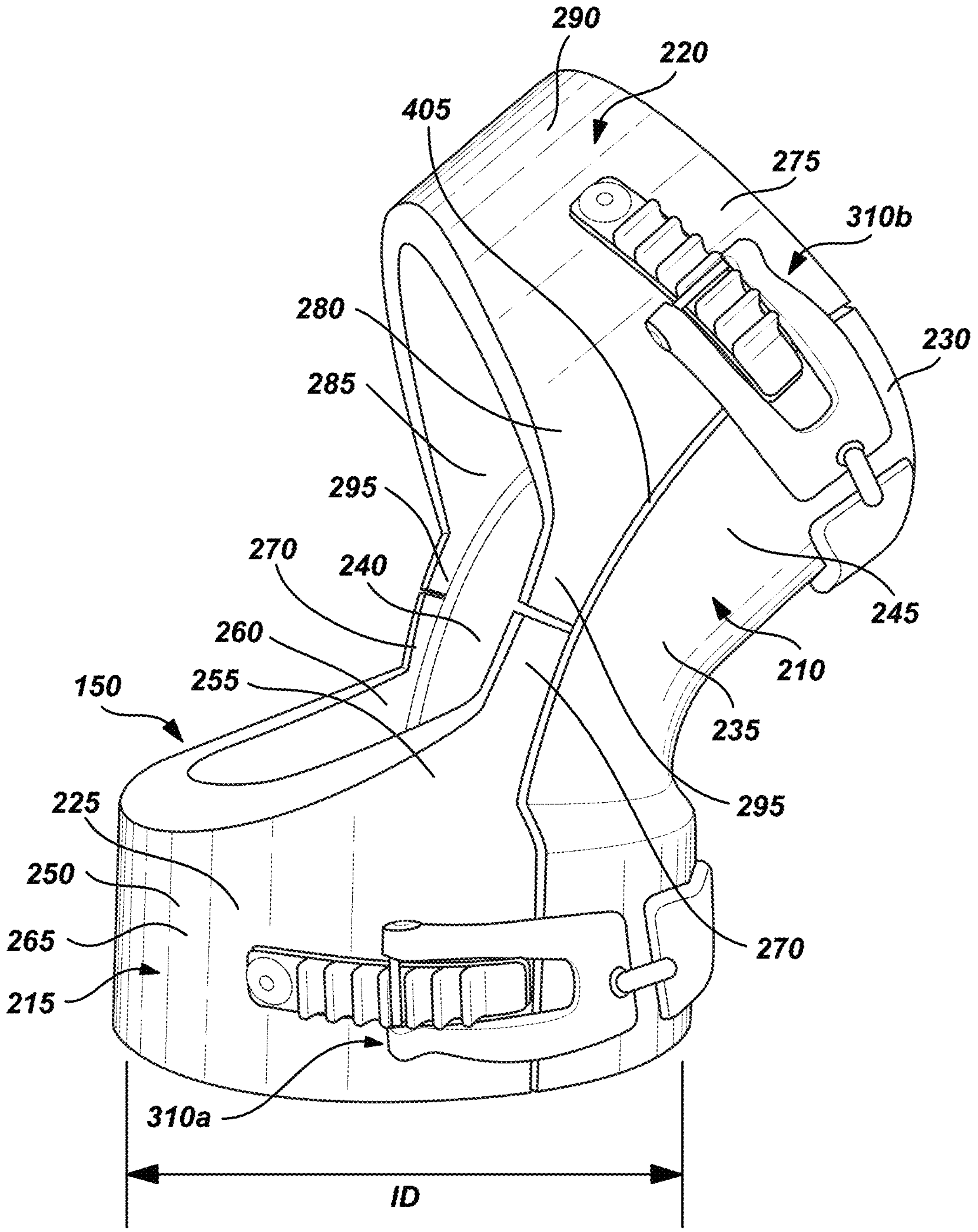
FIG. 4 is another right side, perspective view of the exemplary embodiment of the present invention illustrated in FIG. 1.
Figure 4A:
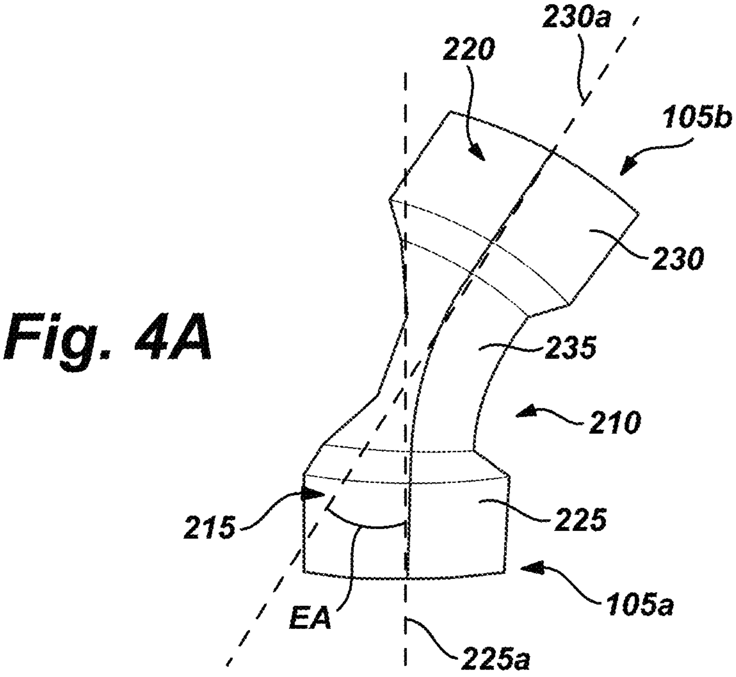
FIG. 4A is a schematic illustration of an exemplary embodiment of the present invention.

Joint member 210 may be a curved member. For example, a longitudinal centerline of a second end component of apparatus 105 may be angled relative to a longitudinal centerline of a first end component of apparatus 105, with intermediate portion 235 being a curved portion disposed between the first and second end components of apparatus 105. For example as illustrated in FIG. 4A, a joint angle EA (e.g., an angle of a joint such as an elbow or a knee) may be formed between a longitudinal centerline 230*a* of a second end component 105*b* of apparatus 105 and a longitudinal centerline 225*a* of a first end component 105*a* of apparatus 105. First end component 105*a* may be formed by first movable member 215 and first end portion 225, and second end component 105*b* may be formed by second movable member 220 and second end portion 230. Joint angle EA may be between about 10 degrees and about 80 degrees, between about 20 degrees and about 70 degrees, between about 30 degrees and about 60 degrees, between about 35 degrees and about 55 degrees, between about 40 degrees and about 50 degrees, between about 42 degrees and about 48 degrees, or any other desired angle. In at least some exemplary embodiments, angle EA may be about 45 degrees. Angle EA may be any other desired angle such as, for example, about 23 degrees or about 68 degrees. Joint member 210 may be configured (e.g., correspondingly curved) to provide a desired value for angle EA. As illustrated in FIG. 4, an interior diameter ID of first end component 105*a* (e.g., and/or second end component 105*b*) may be between about 2" and about 8" (e.g., about 3", about 4", about 5", or about 6"), or any other suitable size for receiving an arm (e.g., or a leg or other hinged joint) of patient 110. Apparatus 105 may be sized (e.g., interior diameter ID may be selected) to accommodate different sizes of patients.

First movable member 215 may be any suitable member for movably attaching (e.g., rotatably attaching) to joint member 210, and for supporting and/or stabilizing a portion of an arm (e.g., or a leg or other hinged joint) of patient 110. For example, first movable member 215 (e.g., and second movable member 220) may serve as an arm stabilizer (e.g., or a leg stabilizer or stabilizer for another hinged joint). First movable member 215 may include a first fastener portion 250 and a first tapered portion 255. First fastener portion 250 and first tapered portion 255 may be integrally formed with each other, or attached to each other via any suitable technique such as mechanical fasteners (e.g., screws and/or bolts), welding, adhesive, snap-fit attachment, press-fit attachment, and/or any other suitable attachment technique. First fastener portion 250 and first tapered portion 255 may form an interior surface 260 at an interior of first movable member 215 that may face an arm (e.g., or a leg or other hinged joint) of patient 110 when patient 110 is wearing apparatus 105. First fastener portion 250 and first tapered portion 255 may also form an exterior surface 265 at an exterior of first movable member 215 that may face away from an arm (e.g., or a leg or other hinged joint) of patient 110 when patient 110 is wearing apparatus 105. Interior surface 260 and exterior surface 265 may thereby be formed on opposite sides of first movable member 215 from each other. First movable member 215 and joint member 210 may be of similar thickness (e.g., up to about 1" or more, between about ⅛" and about ⅞", or any other suitable thickness for stabilizing an arm of patient 110).

First movable member 215 may be a partially curved and tapered member. For example, while first fastener portion 250 of first movable member 215 may not be curved or tapered (e.g., similar to how first end portion 225 of joint member 210 may not be curved or tapered), first tapered portion 255 of first movable member 215 may be curved similarly (e.g., have similar curved edges) to the portion of intermediate portion 235 of joint member 210 that is opposite to first tapered portion 255 when apparatus 105 is in the fully fastened position for example as illustrated in FIGS. 3 and 4. For example, first tapered portion 255 may be curved similarly to intermediate portion 235 so that corresponding edges of first tapered portion 255 and intermediate portion 235 are flush and aligned when apparatus 105 is in the fully fastened position for example as illustrated in FIGS. 3 and 4. First tapered portion 255 may decrease in height in a direction moving away from first fastener portion 250 until reaching first end flanges 270 on both sides of first movable member 215. Based on the exemplary disclosed tapering, first tapered portion 255 may form part of the exemplary disclosed joint aperture described below.

Second movable member 220 may be any suitable member for movably attaching (e.g., rotatably attaching) to joint member 210, and for supporting and/or stabilizing a portion of an arm (e.g., or a leg or other hinged joint) of patient 110, similar to first movable member 215. Second movable member 220 may include a second fastener portion 275 and a second tapered portion 280. Second fastener portion 275 and second tapered portion 280 may be integrally formed with each other, or attached to each other via any suitable technique such as mechanical fasteners (e.g., screws and/or bolts), welding, adhesive, snap-fit attachment, press-fit attachment, and/or any other suitable attachment technique. Second fastener portion 275 and second tapered portion 280 may form an interior surface 285 at an interior of second movable member 220 that may face an arm (e.g., or leg or other hinged joint) of patient 110 when patient 110 is wearing apparatus 105. Second fastener portion 275 and second tapered portion 280 may also form an exterior surface 290 at an exterior of second movable member 220 that may face away from an arm (e.g., or leg or other hinged joint) of patient 110 when patient 110 is wearing apparatus 105. Interior surface 285 and exterior surface 290 may thereby be formed on opposite sides of second movable member 220 from each other. Second movable member 220 may be of a similar thickness as joint member 210 and first movable member 220 for example as described above. In at least some exemplary embodiments, second movable member 220 may be generally similar to and/or a substantial reflection of first movable member 215 taken about a transverse centerline of apparatus 105.

Second movable member 220 may be a partially curved and tapered member. For example, while second fastener portion 275 of second movable member 220 may not be curved or tapered (e.g., similar to how second end portion 230 of joint member 210 may not be curved or tapered), second tapered portion 280 of second movable member 220 may be curved similarly (e.g., have similar curved edges) to the portion of intermediate portion 235 of joint member 210 that is opposite to second tapered portion 280 when apparatus 105 is in the fully fastened position for example as illustrated in FIGS. 3 and 4. For example, second tapered portion 280 may be curved similarly to intermediate portion 235 so that corresponding edges of second tapered portion 280 and intermediate portion 235 are flush and aligned when apparatus 105 is in the fully fastened position for example as illustrated in FIGS. 3 and 4. Second tapered portion 280 may decrease in height in a direction moving away from second fastener portion 275 until reaching second end flanges 295 on both sides of second movable member 220. Based on the exemplary disclosed tapering, second tapered portion 280 may form part of the exemplary disclosed joint aperture described below.

When apparatus 105 is in the fully fastened position with first movable member 215 and second movable member 220 in a closed position and aligned and flush against joint member 210, for example as illustrated in FIGS. 3 and 4, first tapered portion 255 of first movable member 215 and second tapered portion 280 of second movable member 220 may form a joint aperture 150. When apparatus 105 is in the fully fastened position, respective first end flanges 270 and second end flanges 295 may be in contact or nearly in contact (e.g., with a small gap formed between respective first end flanges 270 and second end flanges 295) so that joint aperture 150 is formed that exposes a portion of an arm of patient 110 (e.g., including AC Fossa 115 of patient 110 for example as illustrated in FIGS. 1 and 2) or a leg (e.g., or other hinged joint) of patient 110. Joint aperture 150 may serve as an AC window that allows access to AC Fossa 115. For example, joint aperture 150 may provide access to AC Fossa 115 of patient 110 so that attending personnel may place, remove, adjust, manipulate, and/or troubleshoot an IV device for example as described below.

In at least some exemplary embodiments, structural assembly 200 may be formed from components similar to and/or taken from one or more pipe components such as, for example, structural pipe fittings. For example, structural assembly 200 may be formed from a pipe elbow fitting such as, for example, a PVC or an ABS elbow. The exemplary disclosed pipe elbow may have dimensions and/or a configuration substantially corresponding to a desired angle EA and/or desired dimensions of apparatus 105 (e.g., for example as described above). In at least some exemplary embodiments, joint member 210, first movable member 215, and second movable member 220 may be separated (e.g., cut) from the same pipe fitting or same type of pipe fitting. For example, joint member 210, first movable member 215, and second movable member 220 may be portions of the same pipe fitting elbow such as, for example, a PVC or ABS pipe fitting elbow. In at least some exemplary embodiments, based on modification of an angled PVC tube fitting (e.g., or ABS tube fitting), apparatus 105 may be configured to comfortably secure a patient's elbow joint (e.g., or knee) in a sufficiently extended position (e.g., maintain limb 118 such as an arm or leg (e.g., or another hinged joint) of patient 110 in a straight or extended position) to maintain robust peripheral IV access in the antecubital fossa or similar area.

Fastening assembly 300 may include a plurality of fastening devices such as, for example, fastening device 310*a* and fastening device 310*b*. Fastening devices 310*a* and 310*b* may be similar fastening devices. Fastening devices 310*a* and 310*b* may each include a receiving component and a locking component, with each receiving component configured to receive, attach to, mate with, and/or couple with its respective locking component. Fastening devices 310*a* and/or 310*b* may be ladder and bail systems (e.g., ladder, bail, and lever systems), buckles, latches, hook and loop fasteners, ratchet straps, magnetic fasteners, clips, adhesive fasteners, micrometric closures, double-D rings, and/or any other suitable fasteners for removably fastening components of the exemplary disclosed fastening devices together.

Figure 5:
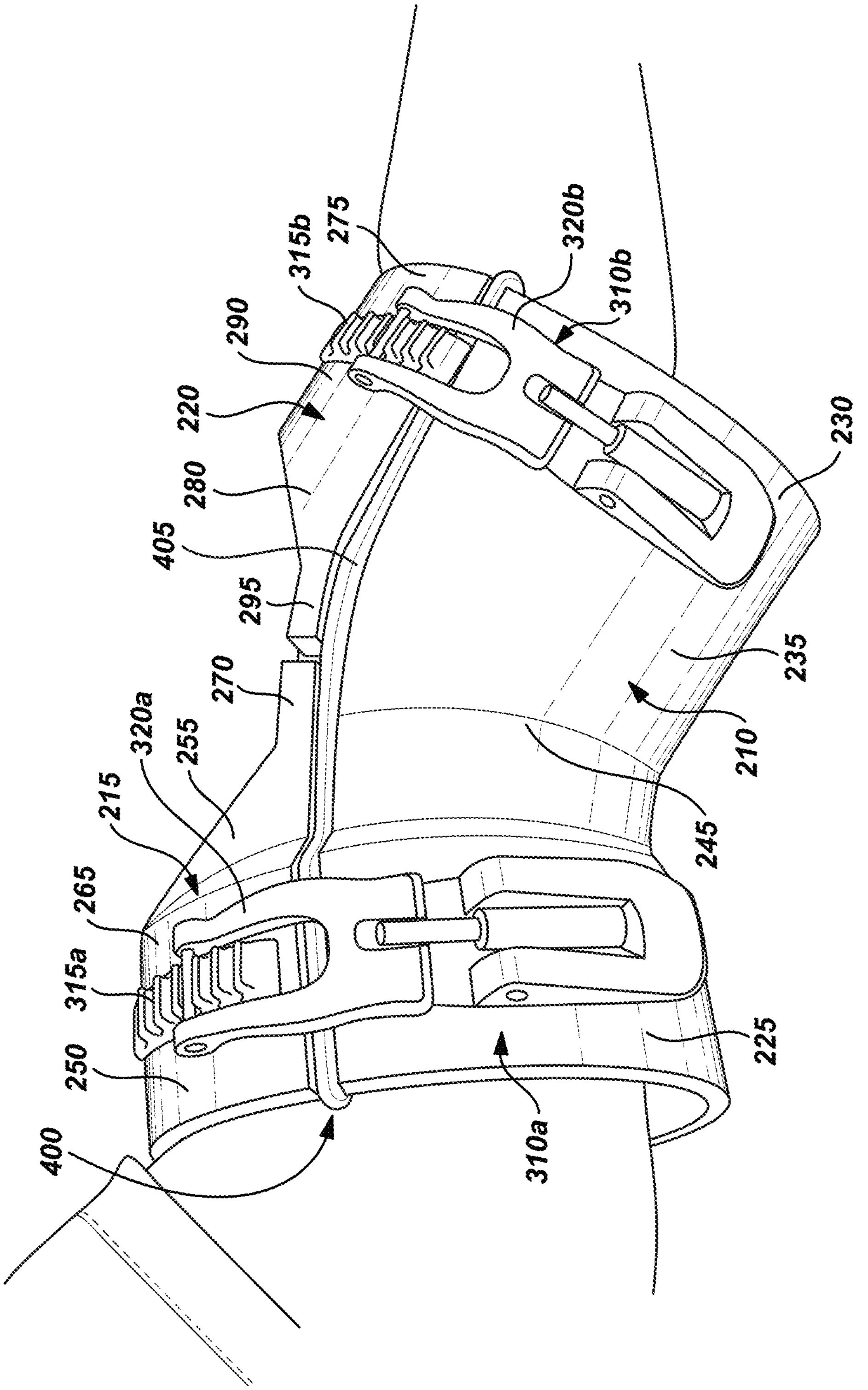
FIG. 5 is a right side, perspective view, from below, of the exemplary embodiment of the present invention illustrated in FIG. 1.

For example as illustrated in FIG. 5, a receiving component 315*a* of fastening device 310*a* may be attached to first fastener portion 250 of first movable member 215 at exterior surface 265 (e.g., or alternatively to joint member 210). A locking component 320*a* of fastening device 310*a* may be attached to first end portion 225 of joint member 210 (e.g., or alternatively to first movable member 215). Receiving component 315*a* and locking component 320*a* of fastening device 310*a* may operate to removably attach first movable member 215 to joint member 210. Similarly, a receiving component 315*b* of fastening device 310*b* may be attached to second fastener portion 275 of second movable member 220 at exterior surface 290 (e.g., or alternatively to joint member 210). A locking component 320*b* of fastening device 310*b* may be attached to second end portion 230 of joint member 210 (e.g., or alternatively to second movable member 220). Receiving component 315*b* and locking component 320*b* of fastening device 310*b* may operate to removably attach second movable member 220 to joint member 210. Components of fastening devices 310*a* and 310*b* may be attached to joint member 210, first movable member 215, and second movable member 220 via mechanical fasteners (e.g., screws and/or bolts), welding, adhesive, snap-fit attachment, press-fit attachment, and/or any other suitable attachment technique. In at least one exemplary embodiment, receiving components 315*a* and 315*b* may be a catch or ladder that may receive a bail portion of respective locking components 320*a* and 320*b* that may include a bail and lever assembly. Any other suitable fastening device may also be used for example as described above.

Figure 6:
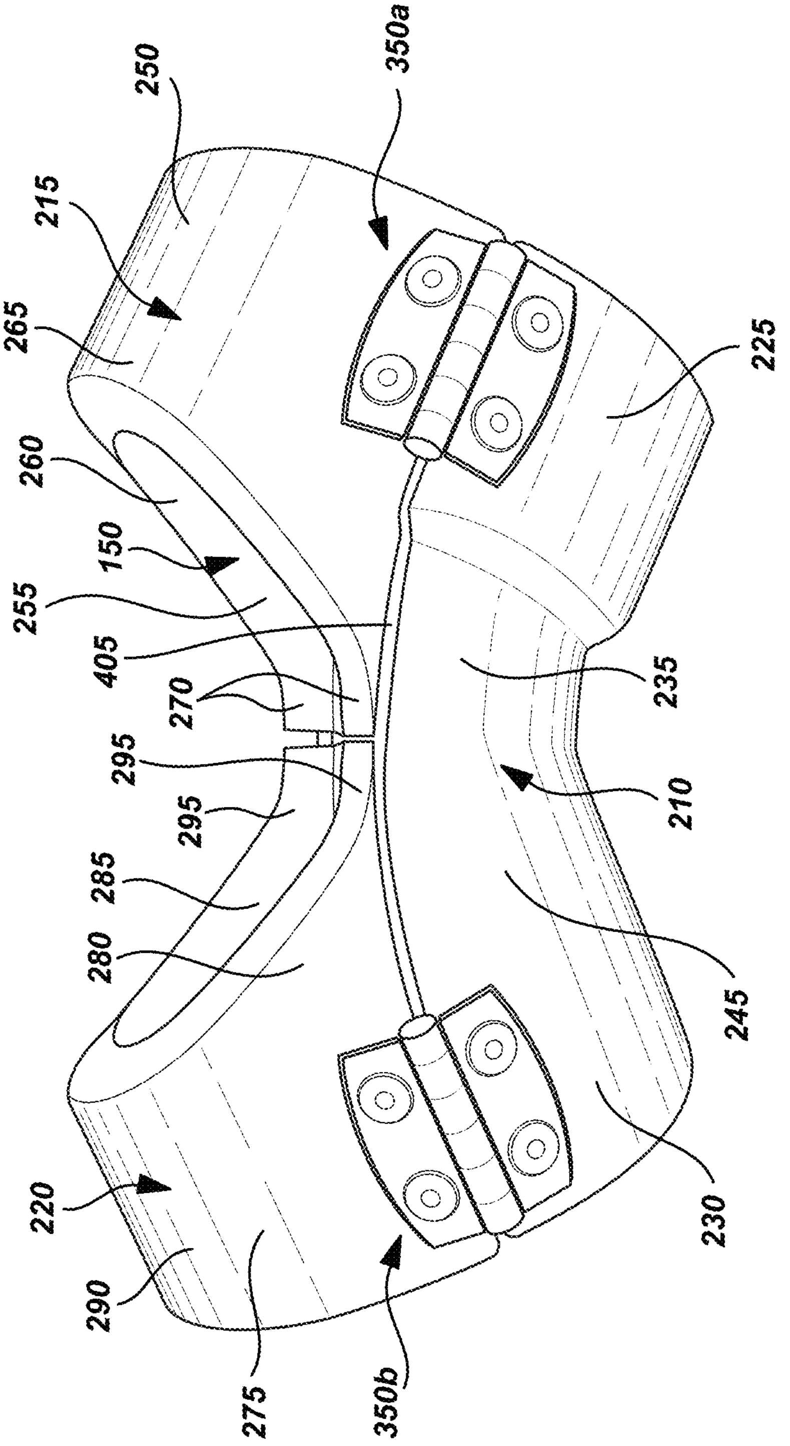
FIG. 6 is a left side, orthogonal view of the exemplary embodiment of the present invention illustrated in FIG. 1.
Figure 7:
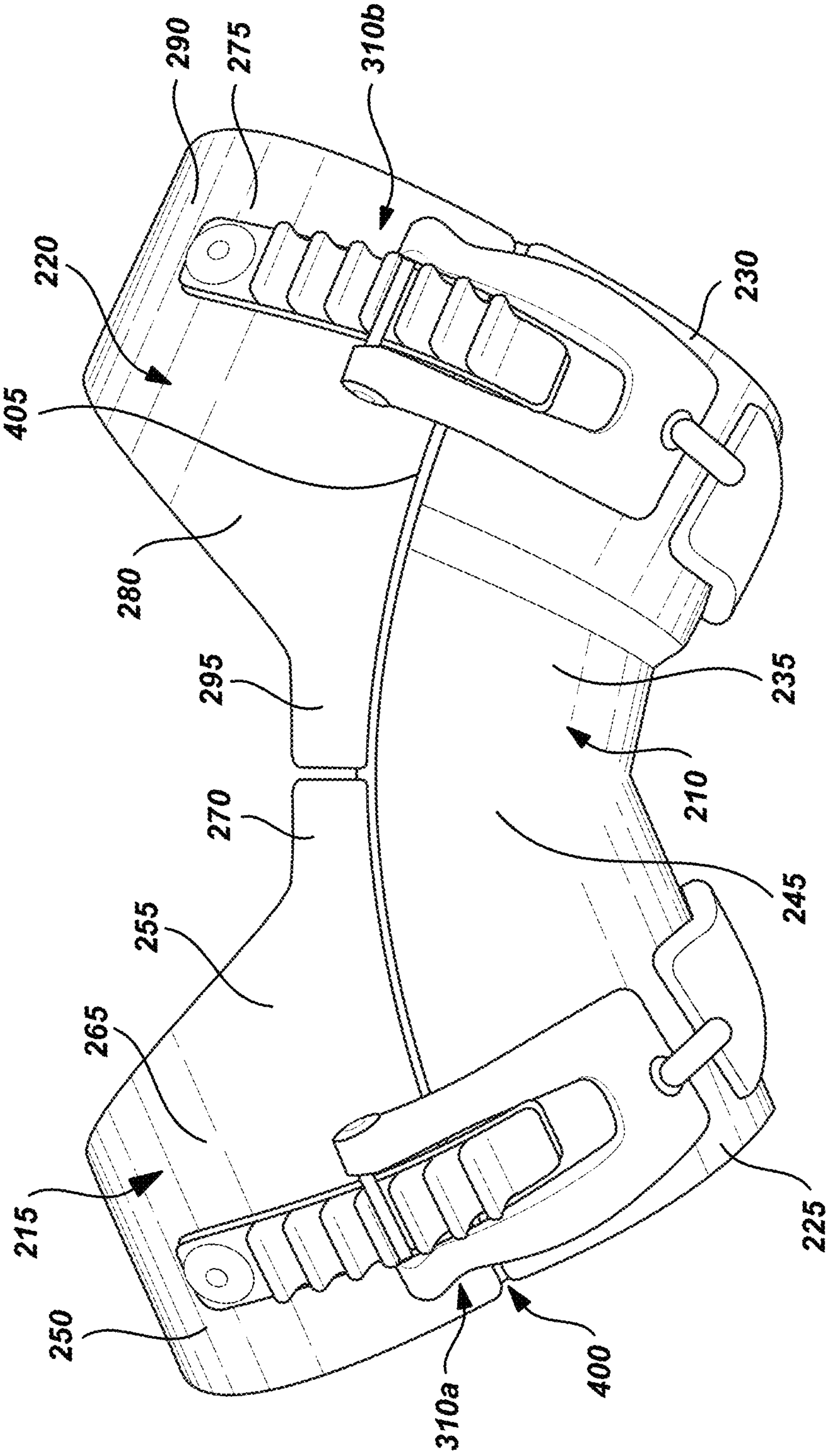
FIG. 7 is a right side, orthogonal view of the exemplary embodiment of the present invention illustrated in FIG. 1.
Figure 8:
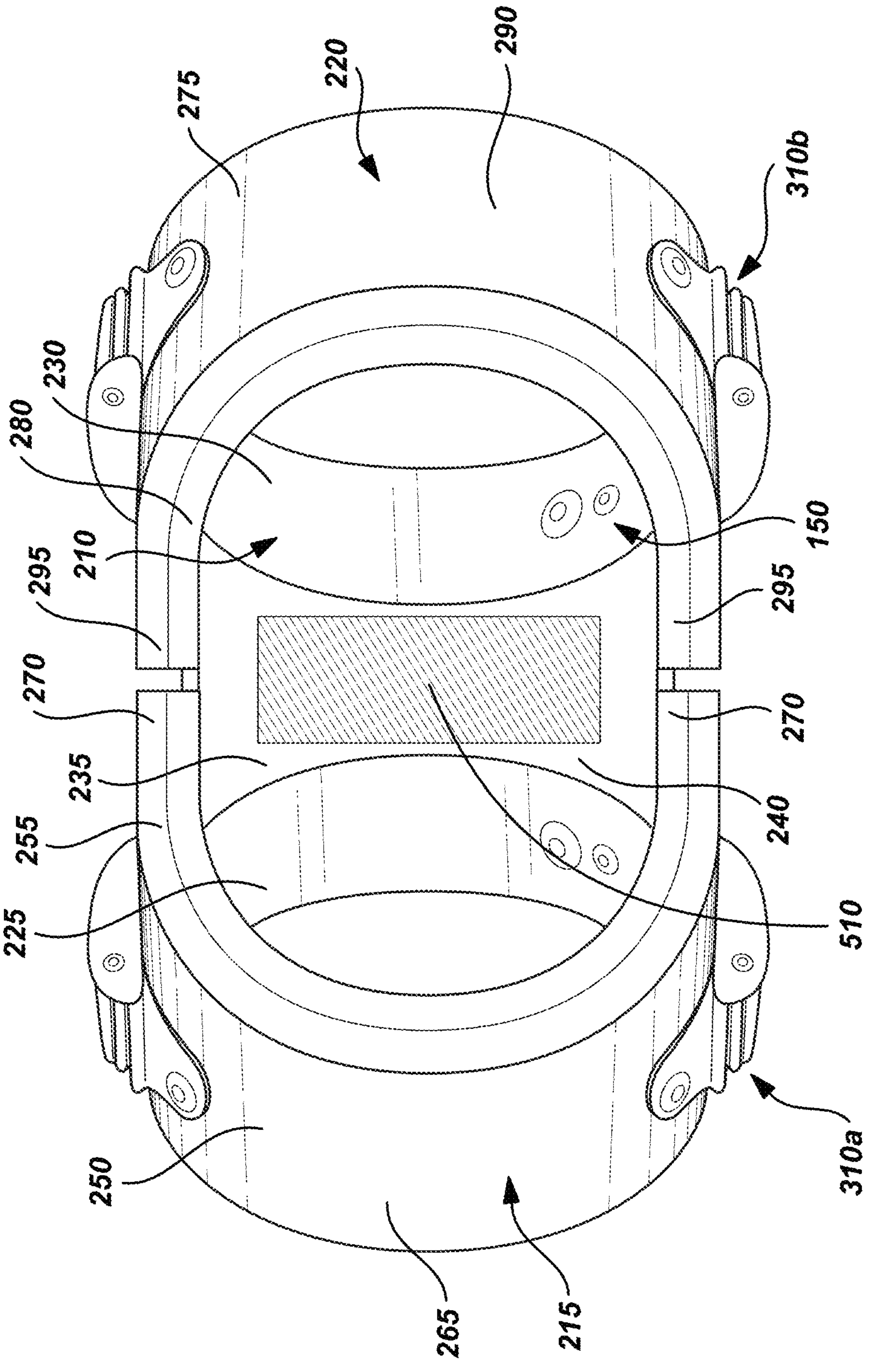
FIG. 8 is a top side, orthogonal view of the exemplary embodiment of the present invention illustrated in FIG. 1.
Figure 9:
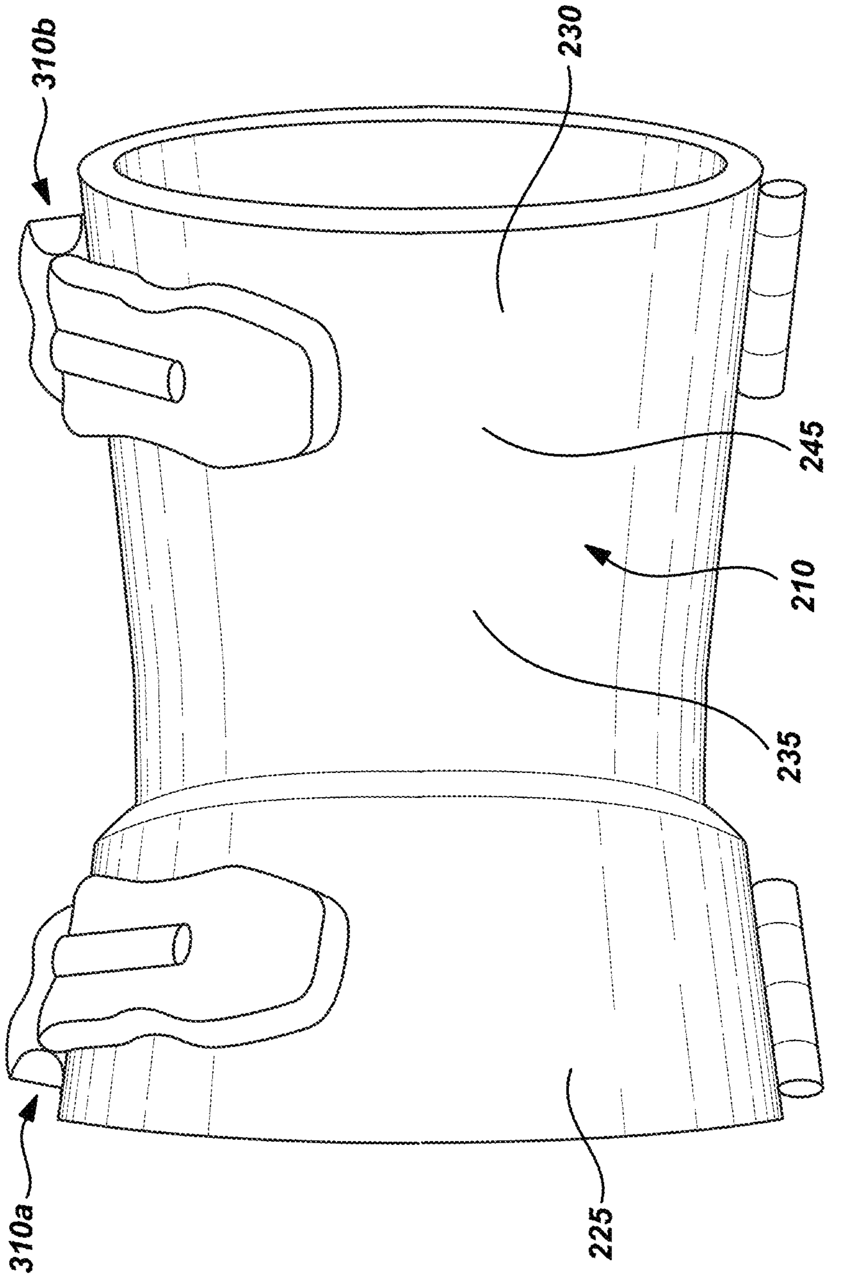
FIG. 9 is a bottom side, orthogonal view of the exemplary embodiment of the present invention illustrated in FIG. 1.
Figure 10:
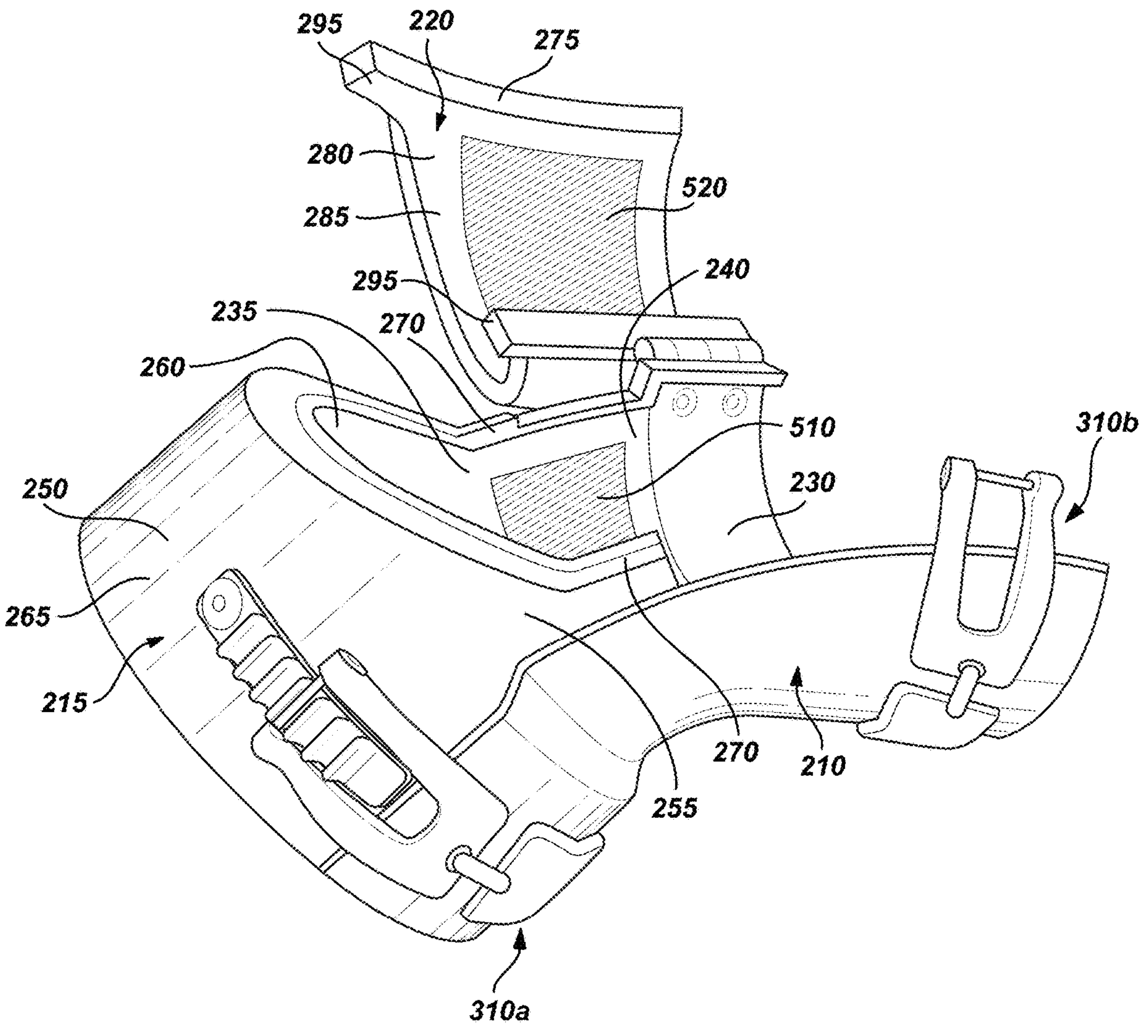
FIG. 10 is a perspective view of the exemplary embodiment of the present invention illustrated in FIG. 1.
Figure 11:
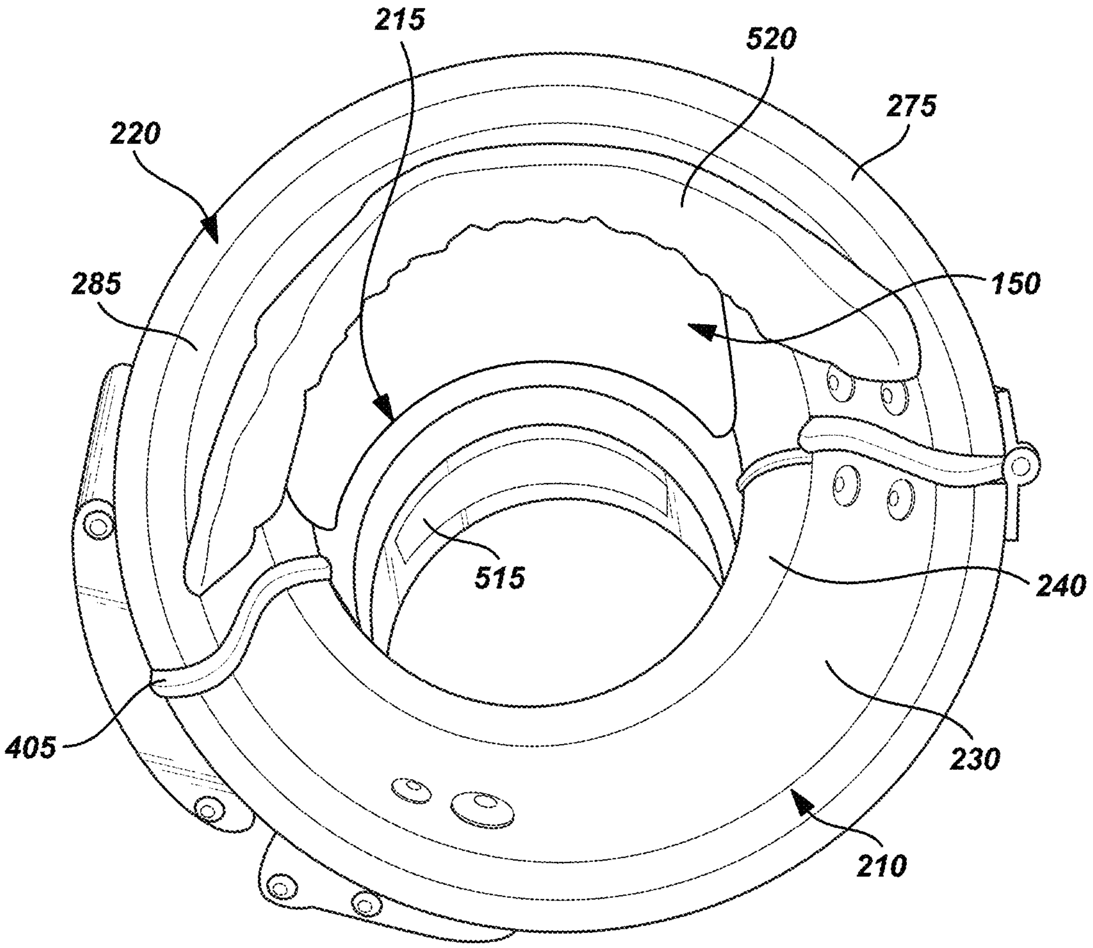
FIG. 11 is a side view, looking through the exemplary disclosed apparatus from one end, of the exemplary embodiment of the present invention illustrated in FIG. 1.

As illustrated in FIG. 6, fastening assembly 300 may also include a plurality of movable connectors such as, for example, movable connectors 350*a* and 350*b*. Movable connectors 350*a* and 350*b* may be disposed on an opposite side of apparatus 105 as fastening devices 310*a* and 310*b*. Movable connectors 350*a* and 350*b* may be any suitable mechanical hinge assemblies (e.g., or other suitable movable assemblies) that may be attached to joint member 210, first movable member 215, and second movable member 220 similarly to as described above regarding attachment of fastening devices 310*a* and 310*b*. In at least some exemplary embodiments, movable connectors 350*a* and 350*b* may allow first movable member 215 and second movable member 220 to rotate relative to joint member 210 (e.g., to rotate open so that patient 110 may put on and remove apparatus 105 from an arm or a leg or another hinged joint of patient 110) when fastening devices 310*a* and 310*b* are unfastened. For example, apparatus 105 may be opened in a clamshell fashion (e.g., first movable member 215 and second movable member 220 may form a clamshell attachment with joint member 210). Alternatively for example, movable connectors 350*a* and 350*b* may be sliding connectors, telescoping connectors, and/or any other suitable connector for moving first movable member 215 and second movable member 220 relative to joint member 210.

Sealing assembly 400 may include any suitable components and/or materials for substantially preventing pinching of an arm (e.g., or a leg or other hinged joint) of patient 110 (e.g., and/or fingers of medical personnel) between movable members 215 and 220 and joint member 210 of structural assembly 200 for example during fastening of apparatus 105 to an arm of patient 110. Sealing assembly 400 may thereby serve as an anti-pinching mechanism. Sealing assembly 400 may include one or more layers 405. Layer 405 may be attached to portions (e.g., edges) of joint member 210, first movable member 215, and second movable member 220 that contact each other when apparatus 105 is in the fully fastened position for example as illustrated in FIGS. 3-7 and 11. Layer 405 may be attached to joint member 210, first movable member 215, and second movable member 220 via any suitable technique. For example, layer 405 may be adhered to edges of joint member 210, first movable member 215, and/or second movable member 220 via any suitable adhesive such as, for example, glue, hot-melt, pressure-sensitive adhesive, rubber, resin, acetate, epoxy, polyurethane, and/or any other suitable adhesive material. Layer 405 may be formed from any suitable material for substantially preventing skin from being caught between movable members 215 and 220 and joint member 210 of structural assembly 200 during fastening of apparatus 105 such as, for example, silicone, natural or synthetic rubber material, felt, gel, flexible polyurethane material, flexible MS polymer material, elastomeric material, and/or any other suitable flexible material.

The exemplary disclosed padding assembly may provide a mechanism by which adjustments (e.g., relatively small adjustments or larger adjustments) may be made to provide suitable fit and stabilization of a patient's arm (e.g., or leg or other hinged joint) in apparatus 105, for example to keep apparatus 105 from slipping off a patient's arm. A first exemplary embodiment of the exemplary disclosed padding assembly is illustrated in FIGS. 3, 8, 10, and 11. The exemplary disclosed padding assembly may include a plurality of pads such as, for example, joint pad 510, first arm pad 515 (e.g., or leg pad or pad for another hinged joint), and second arm pad 520 (e.g., or leg pad or pad for another hinged joint). Joint pad 510 may be attached to intermediate portion 235 of joint member 210 at interior surface 240. First arm pad 515 may be attached to first fastener portion 250 of first movable member 215 at interior surface 260. Second arm pad 520 may be attached to second fastener portion 275 of second movable member 220 at interior surface 285. In at least some exemplary embodiments, pads 510, 515, and 520 may be removably attached to respective joint member 210, first movable member 215, and/or second movable member 220 via hook and loop fasteners, temporary adhesive (e.g., elastomer, tape, silicone sealant), magnetic attachment devices, removably detachable mechanical connectors, and/or any other suitable techniques for removable attachment. Pads 510, 515, and 520 may be thereby removed for cleaning and/or replaced with new pads 510, 515, and 520 when suitable. In at least some exemplary embodiments, pads 510, 515, and 520 may be fixedly attached (e.g., permanently attached) to respective joint member 210, first movable member 215, and/or second movable member 220 via mechanical fasteners (e.g., screws and/or bolts), welding, adhesive, snap-fit attachment, press-fit attachment, and/or any other suitable techniques for permanent attachment.

Pads 510, 515, and 520 may be formed from any suitable elastic and/or flexible material such as, for example, polymer, natural or synthetic rubber, fiber, felt, foam, polyurethane, fabric, and/or any other suitable padding material. Elastic and/or flexible material of pads 510, 515, and 520 may be contained in any suitable container or housing such as a flexible plastic housing, fabric housing, and/or any other suitable flexible container or housing. In at least some exemplary embodiments, pads 510, 515, and 520 may be gel pads formed from hydrogel polymer material. Pads 510, 515, and 520 may have a thickness of between about 2 mm and about 20 mm or more.

Pads 510, 515, and 520 may provide padding at multiple points of an arm (e.g., or a leg or other hinged joint) of patient 110 when patient 110 is wearing apparatus 105. Joint pad 510 may provide padding for an elbow (e.g., or a knee) of patient 110 when wearing apparatus 105. First arm pad 515 may provide padding at either the upper arm (e.g., bicep) or at the lower arm for example at a bottom (e.g., palm side) of the forearm, while second arm pad 520 may provide padding at the other of either the upper arm (e.g., bicep) or the lower arm for example at the bottom (e.g., palm side) of the forearm (e.g., depending on the orientation of apparatus 105, as apparatus 105 may be symmetrical and worn in either orientation). Pads 510, 515, and 520 may similarly provide padding for a leg or other hinged joint of patient 110.

Figure 12:
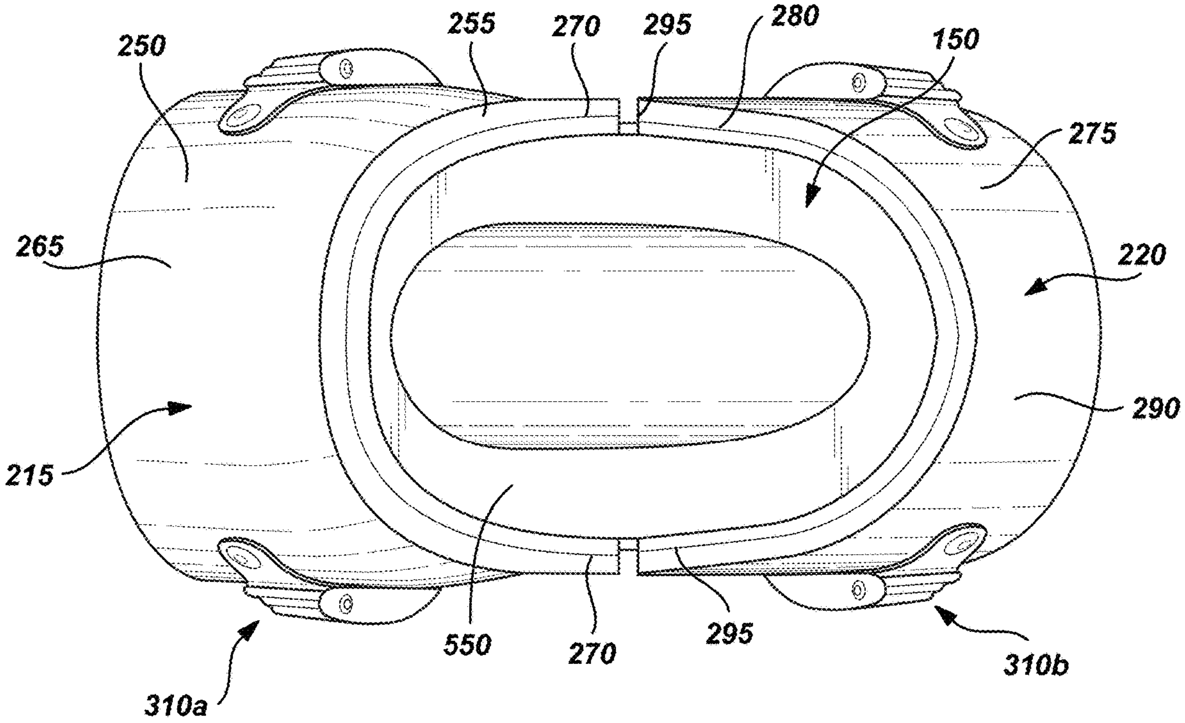
FIG. 12 is a top side perspective view of an exemplary embodiment of the present invention.
Figure 13:
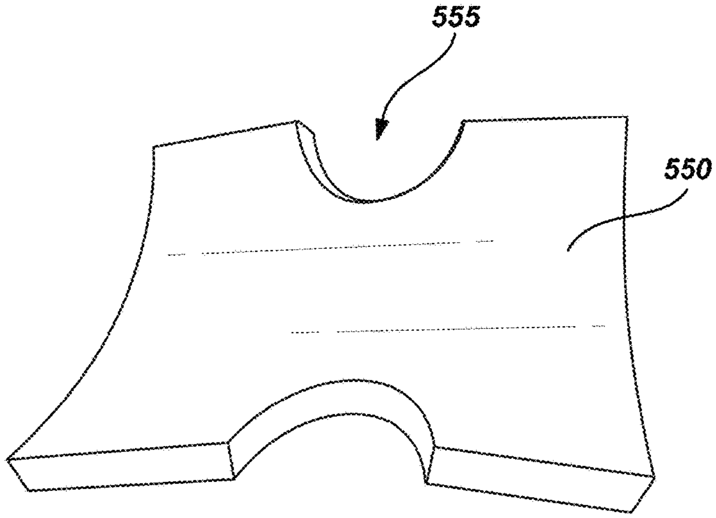
FIG. 13 is a top left perspective view of an exemplary embodiment of the present invention.

A second exemplary embodiment of the exemplary disclosed padding assembly is illustrated in FIGS. 12 and 13. The exemplary disclosed padding assembly may include one or more pads such as one or more filler pads 550. Filler pad 550 may be a layer of padding that may be formed (e.g., cut or dimensioned) to fit a part of apparatus 105 (e.g., at one or more of the exemplary disclosed interior surfaces) or substantially all of apparatus 105. Filler pad 550 may be disposed between an arm (e.g., or a leg or other hinged joint) of patient 110 and the exemplary disclosed interior surfaces of structural assembly 200 when patient 110 is wearing apparatus 105. For example, filler pad 550 may be a single layer of padding dimensioned to receive an arm (e.g., or leg or other hinged joint) of patient 110 and also fit into apparatus 105 when patient 110 is wearing apparatus 105 in the fully fastened position. For example, filler pad 550 may include one or more cutouts or recesses 555 configured to correspond to joint aperture 150 so that filler pad 550 does not block joint aperture 150 when apparatus 105 is worn with filler pad 550. Filler pad 550 may be a foam sleeve (e.g., a foam sizing sleeve). Filler pad 550 may be formed from any suitable elastic or flexible material such as, for example, foam (e.g., polyurethane foam, polyethylene foam, and/or polystyrene foam), neoprene, foam cell, inflated cushioning, and/or any other suitable flexible material (e.g., filler material). In at least some exemplary embodiments, filler pad 550 may include one or more pneumatic sizing balloons. One or more filler pads 550 may be used as an alternative to pads 510, 515, and/or 520, or in combination with pads 510, 515, and/or 520. Filler pad 550 may have a thickness of between about 2 mm and about 20 mm or more. One or more filler pads 550 may be removably attachable and/or fixedly attached to joint member 210, first movable member 215, and/or second movable member 220 similar to as described above regarding pads 510, 515, and 520. One or more filler pads 550 may also be placed between a patient's arm (e.g., or leg or other hinged joint) and the exemplary disclosed interior surfaces of structural assembly 200 without attachment to interior surfaces of joint member 210, first movable member 215, and/or second movable member 220.

The exemplary disclosed padding assembly may provide an anti-slip mechanism. The exemplary disclosed padding assembly may be used in filling a distal end of apparatus 105 to the ventral forearm (e.g., to keep apparatus 105 from sliding off the patient's arm or leg or other hinged joint). Apparatus 105 may provide for tourniquet integration in securing the ventral aspect of the arm to the proximal end. Pneumatic components (e.g., balloons) may also be used at the patient's forearm and/or upper arm to keep apparatus 105 from slipping. Apparatus 105 may also provide for BP sphygmomanometer integration.

Figure 5A:
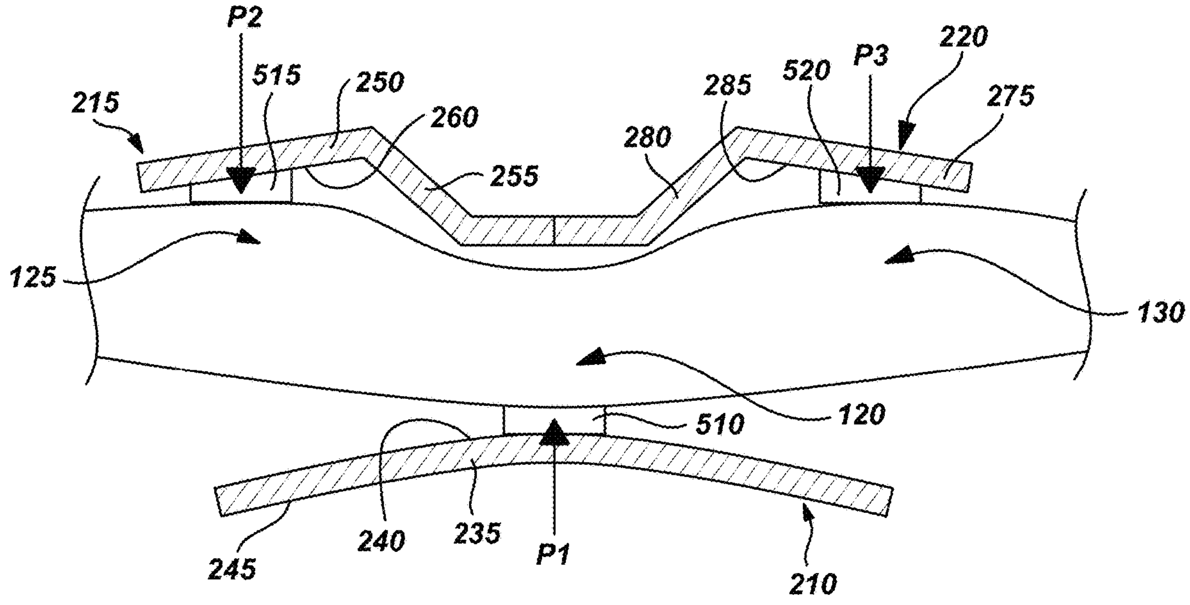
FIG. 5A is a schematic illustration of an exemplary embodiment of the present invention.

Apparatus 105 may provide multiple points of contact to exert mechanical advantage (e.g., significant mechanical advantage) over the elbow joint (e.g., or knee), which may maintain sufficient extension at the elbow (e.g., maintain elbow extended at or near 180 degrees) or knee. Beneficially, these exemplary disclosed points of contact on an arm (e.g., or leg or other hinged joint) of patient 110 may not restrict blood flow from the accessed blood vessel (e.g., at joint aperture 150, for example AC Fossa 115) back to the patient's more central circulation and heart. In at least some embodiments, there may be three points of contact (e.g., or any other suitable number of points of contact such as, for example, two or four or more points of contact). For example as illustrated in FIG. 5A, a first point of contact P1 may be at intermediate portion 235 of joint member 210 at interior surface 240 (e.g., where joint pad 510 may be attached in some embodiments, or a portion of filler pad 550). Also for example, a second point of contact P2 may be at first fastener portion 250 of first movable member 215 at interior surface 260 (e.g., where first arm pad 515 may be attached in some embodiments, or a portion of filler pad 550). Further for example, a third point of contact P3 may be at second fastener portion 275 of second movable member 220 at interior surface 285 (e.g., where second arm pad 520 may be attached in some embodiments, or a portion of filler pad 550). First point of contact P1 may contact a joint 120 (e.g., an elbow or a knee) of patient 110. Second point of contact P2 may contact an upper arm 125 (e.g., bicep) of patient 110. Third point of contact P3 may contact a lower arm 130 (e.g., at a bottom or palm side of the forearm) of patient 110. Apparatus 105 may also be reversed in orientation (e.g., reversed 180 degrees) so that third point of contact P3 may contact upper arm 125 (e.g., bicep) of patient 110, and second point of contact P2 may contact lower arm 130 (e.g., at the bottom or palm side of the forearm) of patient 110. Also for example when limb 118 of patient 110 is received in apparatus 105, joint member 210 may provide first point of contact P1 against joint 120, first movable member 215 may provide second point of contact P2 against a first portion of limb 118 spaced a first direction from joint 120, and second movable member 220 may provide third point of contact P3 against a second portion of limb 118 spaced a second direction from joint 120 that is opposite to the first direction. Apparatus 105 may similarly be used to substantially prevent extension (e.g., flexion) of a patient's knee (e.g., to access the popliteal fossa similarly to the AC fossa, or to access the flexor surface of any hinged joint).

Figure 4B:
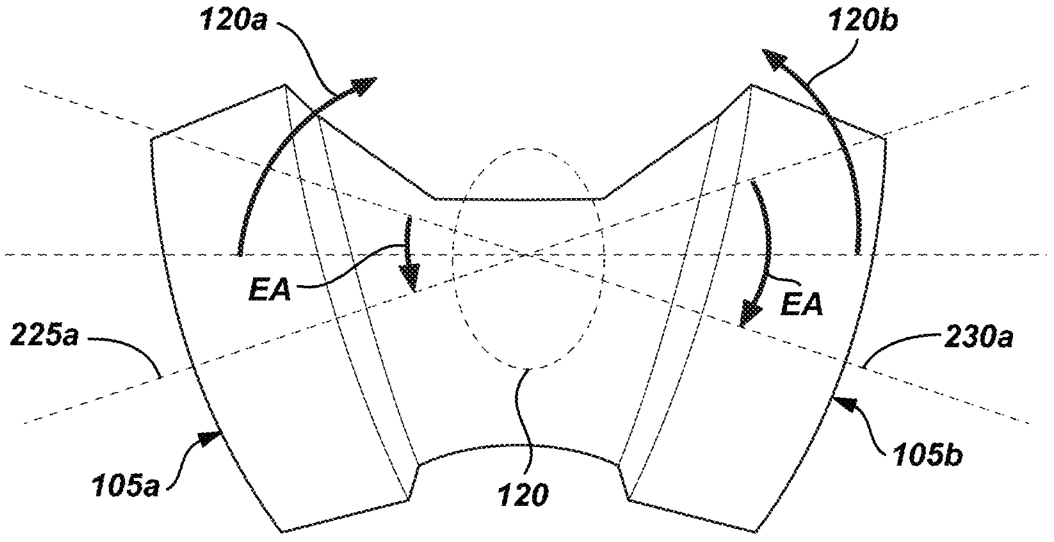
FIG. 4B is another schematic illustration of an exemplary embodiment of the present invention.

Apparatus 105 may be configured to be bent in a direction that is opposite to a direction of elbow flexion (e.g., or knee or other joint flexion) of patient 110 when apparatus 105 is worn by patient 110. For example as illustrated in FIGS. 4A, 5, and 5A, apparatus 105 may be angled at angle EA. Angle EA may form an angle opposing a direction of flexion (e.g., bending) of joint 120 of patient 110 (e.g., angle EA may be opposite to a direction of flexion rotation of a patient limb about joint 120). For example as schematically illustrated in FIG. 4B, apparatus 105 may be angled at angle EA that may be opposite to (e.g., away from) joint flexion directions 120*a* and 120*b* of a patient's limb, which may be received in apparatus 105, about joint 120. That is, for example, apparatus 105 may be angled opposite to (e.g., away from) a flexion direction of limb 118 of patient 110 when patient 110 is wearing apparatus 105. Angle EA may thereby be opposite to a flexion angle of joint 120. This exemplary disclosed configuration may help to exert mechanical advantage (e.g., significant mechanical advantage) over the elbow joint (e.g., or knee joint), which may maintain sufficient extension at the elbow (e.g., in addition to and/or in combination with points of contact P1, P2, and P3) or knee. This exemplary disclosed configuration of apparatus 105 may help apparatus 105 to stay in place on a patient's arm (e.g., or leg or other hinged joint), for example when the arm is disposed perpendicular to the ground (e.g., when a patient is lying on a stretcher or a hospital bed).

In at least some exemplary embodiments, the exemplary disclosed mechanical advantage may minimize the possibility of patients hurting themselves by exerting force against apparatus 105 itself, based on the exemplary disclosed configuration of apparatus 105 (e.g., angle EA and/or points of contact P1, P2, and P3). The exemplary disclosed mechanical advantage may substantially prevent patient injury during procedures in which a patient may transition between a relatively deeper state of sedation and a relatively lighter state of sedation (e.g., when a patient often will reflexively flex their arms about their elbow).

In at least some exemplary embodiments, apparatus 105 may provide antecubital protection (e.g., "antecubital armor) by improving a stability of peripheral intravenous access in the antecubital fossa. Apparatus 105 may provide such antecubital protection for patients undergoing a sedated intervention. Apparatus 105 may stabilize a patient's arm (e.g., or leg or other hinged joint) to comfortably maintain the patient's elbow (e.g., or knee) in an extended position. Apparatus 105 may reduce (e.g., significantly reduce) the risk of malfunction of peripheral intravenous access in the antecubital fossa, which may allow for regularly using the AC fossa to establish and/or maintain peripheral IV (PIV) access for patients in multiple care settings. This may be done without ultrasound guided PIVs, central venous access, mid lines, and/or similar techniques.

In at least some exemplary embodiments, apparatus 105 may be utilized in an outpatient non-surgical procedural setting (e.g., endoscopy suite, imaging center, heart catheterization lab, angiography suite, and/or similar settings), for which quickly gaining robust peripheral IV access may be an integral part of a given procedure or service. Also for example, apparatus 105 may be used in the emergency department, intensive care unit, medical floor, and/or similar settings for securing short-term, relatively larger bore peripheral access for a specific directed therapy.

In at least some exemplary embodiments, a coating may be applied to the exemplary disclosed surfaces of apparatus 105 to facilitate cleaning. For example, a rubberized or plasticized coating may be applied to surfaces (e.g., exemplary disclosed exterior and/or interior surfaces) of apparatus 105. The exemplary disclosed coating may provide for durability of apparatus 105 so that apparatus 105 may be able to tolerate repeated (e.g., years of) use and regular cleaning.

In at least some exemplary embodiments, apparatus 105 may substantially prevent patients from harming themselves unintentionally due to the patient's inability to exert a meaningful amount of force against apparatus 105 (e.g., despite the relative comfort in wearing apparatus 105). Joint aperture 150 may allow a medical provider to confirm that an IV apparatus is suitably functioning while apparatus 105 is worn (e.g., without removing apparatus 105) by viewing the IV apparatus through joint aperture 150. Apparatus 105 may also serve as a scaffold to provide for reliable measurement of blood pressure and oxygen saturation (e.g., and other indicators).

In at least some exemplary embodiments, apparatus 105 may provide an easy-to-use and easy-to-secure stabilization device that may be attached to a patient's arm (e.g., or leg or other hinged joint) just before sedation begins. Apparatus 105 may be removed before patients are awake, or patients can readily put on and take off apparatus 105 on their own. Joint aperture 150 may be used to maintain view of an IV apparatus to facilitate troubleshooting of the IV apparatus without removing apparatus 105. Apparatus 105 may serve as a short term device to accomplish a goal involving, for example, a procedure, imaging, obtaining units of blood, providing IVF, and/or any other suitable use. Apparatus 105 may provide a portable-use device in multiple settings. Apparatus 105 may be used with difficult-access patients alternatively or before mid-line or PICC is used. Apparatus 105 may provide for immobilization involving BP monitoring (sphygmo-manometry), pulse oximetry, and/or similar uses.

Apparatus 105 may be sized for various patient types and/or uses (e.g., including sizing of interior diameter ID to be 3", 4", 5", 6", or any other desired size). For example, apparatus 105 may be sized for use in pediatric care, adult care, large adult care, bariatric care, and/or any other suitable type of care. A size of first end component 105*a* (e.g., first movable member 215) may be sized differently from second end component 105*b* (e.g., second movable member 220). Inserts and/or padding such as pads 510, 515, and 520, filler pad 550, spring components, pneumatic components (e.g., balloons), elastic or flexible components (e.g., silicone bands), mini-scissor lifts, and/or any other similar components may be used or considered in sizing apparatus 105.

In at least some exemplary embodiments, the exemplary disclosed fasteners of apparatus 105 may be mechanical fasteners. For example, such fasteners may include pop rivets with washers, screws with tips ground off, screws with nuts, sunken (e.g., zero profile) fasteners, fasteners with countersunk washers, and/or any other suitable fasteners. One or more flexible sleeves (e.g., flexible fabric sleeves) may be used on one or both sides of joint aperture 150.

Any suitable peripheral (e.g., add-on devices) may be used with apparatus 105. For example, apparatus 105 may be used with sphygmomanometry devices that may be disposed adjacent to apparatus 105 (e.g., adjacent to second end component 105*b*) to facilitate fit of apparatus 105 on a patient's arm. Pulse Oximetry devices may be used with apparatus 105 for determining an Hg content of blood refluxed from an IV catheter. Apparatus 105 may also be used with additional tools or devices for other IV access points (e.g., of a given patient).

The exemplary disclosed apparatus may utilize any suitable configuration and/or materials for providing the exemplary disclosed stabilization of a patient's arm. Any suitable frame may be used to provide the exemplary disclosed stabilization. For example, a frame including plastic pipe (e.g., similar to the apparatus 105) with steel reinforcement may be used. Also for example, a plastic board with straps or similar devices to affix a patient's arm may be used such as, for example, hook and loop fasteners, ratchet straps, and/or similar fasteners. Further for example, parallel steel rods with crossbars as arm stabilizers and/or elbow stabilizers may be used. For example, a scaffold (e.g., a structural metal surgical scaffold such as a stainless steel surgical scaffold) may be used for the exemplary disclosed cradle and stabilizers. The exemplary disclosed apparatus may include steel members (e.g., parallel steel rods). For example, two metal members (e.g., steel bars or rods) may be connected to each other at both ends of the exemplary disclosed apparatus, with adjustable sizing provided by tightening of an elbow support attached to (e.g., hanging from) intermediate or middle portions of the two metal members.

The exemplary disclosed apparatus may be used in various orientations. For example, based on symmetry of the apparatus in at least some exemplary embodiments, the device may be worn in varying reversible orientations (e.g., with the exemplary disclosed fastening devices facing toward the patient's body in some orientations, and away from the patient's body in other orientations). The exemplary disclosed apparatus may thereby provide increased ease of use (e.g., by reversibility of the apparatus).

The exemplary disclosed system, apparatus, and method may provide for effective PIV in the AC fossa, which can be performed by either experienced or inexperienced medical staff. For example, the exemplary disclosed system, apparatus, and method may allow for effective PIV in the AC fossa in place of relatively more difficult tasks such as central access that can carry increased risk for venous thrombosis, infection, and placement-related complications. Similarly, the exemplary disclosed system, apparatus, and method may allow for effective PIV in the AC fossa, which may avoid increased central line association bloodstream infection (CLABSI) rates associated with more difficult tasks such as central access.

The exemplary disclosed system, apparatus, and method may be used during procedures, imaging, emergency department use, ICU or medical floor care, or similar uses to gain reliable IV access to facilitate a targeted intervention. Such simple and effective access may be used to provide anesthesia for a procedure, deliver a bolus of contrast agent for a CT scan or angiogram, deliver IV hydration through a relatively large bore IV, provide a unit of blood in a patient, or similar uses.

The exemplary disclosed system, apparatus, and method may also be used for orthopedic procedures, pre or post operative care, and/or other uses when maintaining 180 degree extension at the elbow (e.g., or knee or other hinged joint) of a patient is desirable. Apparatus 105 may also be used to substantially prevent extension (e.g., flexion) of a patient's knee, similar to preventing flexion at the elbow (e.g., to access the popliteal fossa similarly to the AC fossa). Apparatus 105 may also be used for a prolonged episode of phlebotomy (e.g., timed blood draws such as glucose tolerance tests and dexamethasone suppression tests). Apparatus 105 may also be used to help substantially prevent patients from touching their face with their hands or fingers. Apparatus 105 may also be used for reliable intraprocedural vital sign measurement (e.g., blood pressure, oxygen saturation, and/or other suitable measurement).

The exemplary disclosed system, apparatus, and method may be used in any suitable application for providing IV access. For example, the exemplary disclosed system, apparatus, and method may be used in any suitable application involving effective peripheral intravenous access (PIV) in the AC fossa. The exemplary disclosed system, apparatus, and method may be used in any suitable application in which it is desirable to maintain substantially 180 degree extension at the elbow or knee. For example, the exemplary disclosed system, apparatus, and method may be used in any suitable application involving pre- or post-operative medical care (e.g., or procedure such as a prolonged episode of phlebotomy) during which maintaining substantially 180 degree extension at the elbow or knee is desirable.

Figure 16:
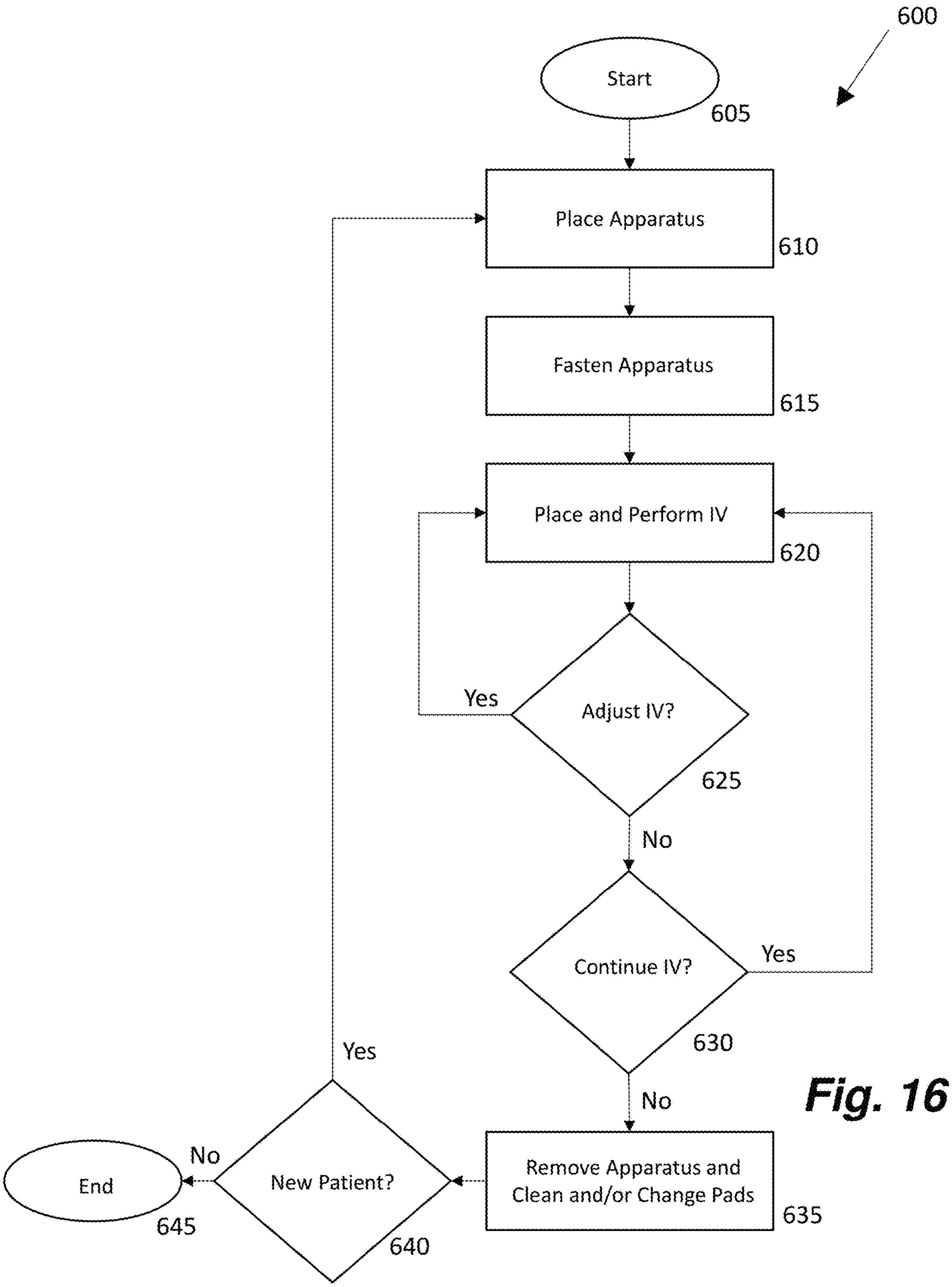
FIG. 16 illustrates an exemplary process of using at least some exemplary embodiments of the present disclosure.

FIG. 16 illustrates an exemplary process of using the exemplary disclosed system and apparatus. Process 600 begins at step 605. At step 610, apparatus 105 may be placed. Patient 110 may place apparatus 105 in an unfastened position at a joint location on the patient's own, or medical personnel may assist patient 110 or place apparatus 105 in the unfastened position without patient assistance. Placement may be intuitive to patient 110 and/or attending medical personnel (e.g., apparatus 105 may be readily understood and correct positioning at joint 120 may be relatively easy to achieve).

Figure 14:
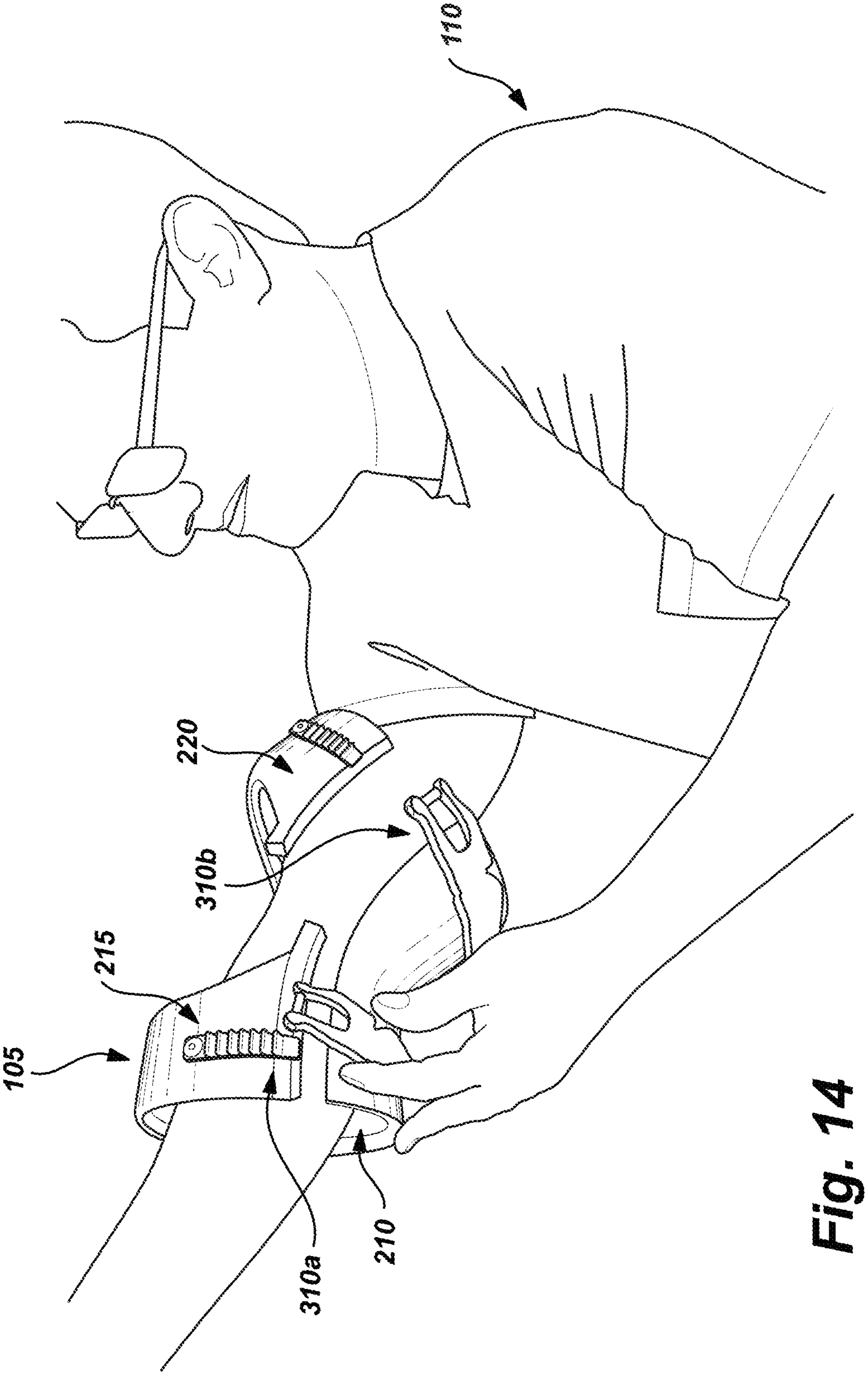
FIG. 14 is a side perspective view of the exemplary embodiment of the present invention illustrated in FIG. 1.
Figure 15:
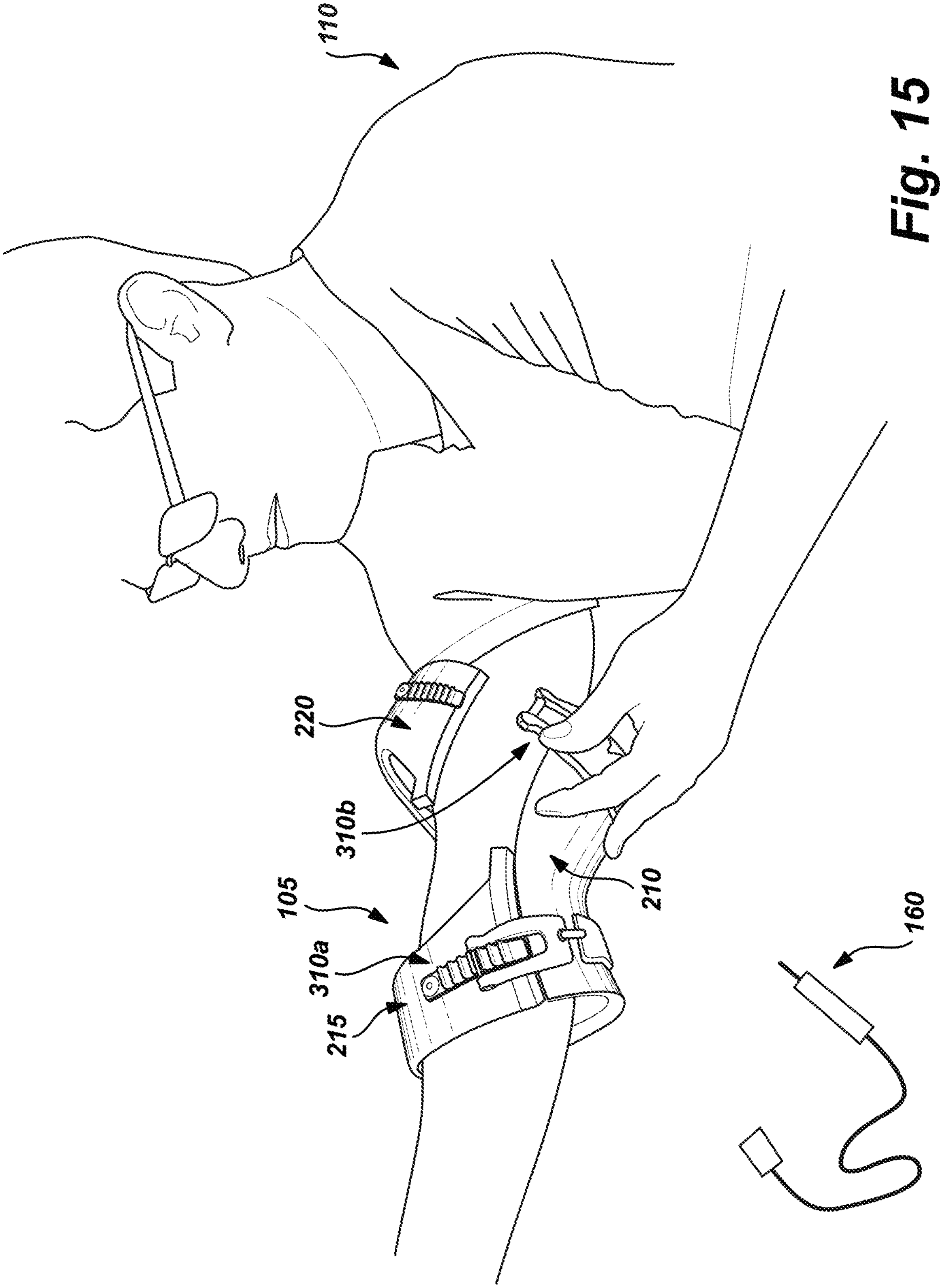
FIG. 15 is a side perspective view of the exemplary embodiment of the present invention illustrated in FIG. 1.

At step 615, apparatus 105 may be fastened. As illustrated in FIG. 14, an arm (e.g., or leg or other hinged joint) of patient 110 may be placed in joint member 210 and first movable member 215 may be fastened to joint member 210 via operation of fastening device 310*a* (e.g., so that apparatus 105 is in a partially fastened position). Then, as illustrated in FIG. 15, second movable member 220 may be fastened to joint member 210 via operation of fastening device 310*b* (e.g., so that apparatus 105 is in a fully fastened position). Alternatively, second movable member 220 may be fastened first, followed by first movable member 215. In the case in which padding such as pads 510, 515, and/or 520 and/or filler pad 510 are not yet attached, such padding may be attached to structural assembly 200 and/or placed in structural assembly 200, for example as described above, prior to placing apparatus 105 on patient 110 (e.g., prior to step 610).

At step 620, an intravenous device 160 may be placed by medical personnel and peripheral intravenous access (PIV) may be performed. For example, intravenous device 160 may be placed at the opening provided by joint aperture 150. For example, PIV may be performed at AC fossa 115 on an arm of patient 110 (e.g., or alternatively PIV may be performed at a leg or another hinged joint of patient 110). Intravenous device 160 may be inserted in patient 110 either before or after movable members 215 and 220 are fastened to joint member 210. PIV may be provided via intravenous device 160 as medically suitable. Apparatus 105 may effectively limit the movement of the limb 118 (e.g., arm or leg or other hinged joint) of patient 110 during PIV as described above (e.g., based on mechanical advantage provided by angle EA and/or points of contact P1, P2, and/or P3) so that there is substantially no flexion about joint 120 of patient 110.

At step 625 it may be determined by attending medical personnel whether intravenous device 160 is to be adjusted based on the medical care circumstances. If intravenous device 160 is to be adjusted, process 600 returns to step 620. Medical personnel may readily adjust intravenous device 160 via the opening of joint aperture 150 without moving or manipulating apparatus 105. For example, intravenous device 160 may be adjusted while apparatus 105 is still actively maintaining an extended position of a patient's arm (e.g., or leg or other hinged joint), so that PIV malfunction is substantially avoided (e.g., apparatus 105 may remain in the fully fastened position with both movable members 215 and 220 fastened to joint member 210). If intravenous device 160 is not to be adjusted, process 600 proceeds to step 630.

At step 630, it may be determined whether or not PIV is to be continued. If PIV is to be continued, process 600 returns to step 620. If PIV is not to be continued, process 600 proceeds to step 635. As many iterations as desired of steps 610 through 630 may be performed. If PIV of patient 110 is not to be continued, process 600 proceeds to step 635.

At step 635, intravenous device 160 may be removed from patient 110. For example, apparatus 105 may be removed from patient 110 by following the reverse order of step 615. Second movable member 220 may be unfastened from joint member 210 via operation of fastening device 310*b* (e.g., so that apparatus 105 is in the partially fastened position). First movable member 215 may be unfastened from joint member 210 via operation of fastening device 310*a* (e.g., so that apparatus 105 is in the unfastened position). Alternatively, first movable member 215 may be unfastened first, followed by second movable member 220. Medical personnel may remove apparatus 105 when patient 110 is still sedated, or alternatively apparatus 105 may be removed by medical personnel or by patient 110 when patient 110 awakens (e.g., or when patient 110 is ready to remove apparatus 105, if patient 110 is not sedated). For example, despite the propensity of apparatus 105 to stay in place, apparatus 105 may be readily removable when it is no longer to be utilized. For example, patient 110 can readily remove apparatus 105 when patient 110 desires (e.g., apparatus 105 may not be a restraint).

Apparatus 105 may be cleaned by any suitable technique. Pads 510, 515, and/or 520 and/or filler pad 510 may be cleaned while still attached to structural assembly 200, detached from structural assembly 200 and cleaned, and/or detached from structural assembly 200 and replaced with new padding.

At step 640, it may be determined whether apparatus 105 is to be utilized on a new patient. If apparatus 105 is to be utilized on a new patient, process 600 returns to step 610. As many iterations as desired of steps 610 through 640 may be performed. If apparatus 105 is not to be utilized on a new patient, process 600 ends at step 645.

The invention includes other illustrative embodiments ("Embodiments") as follows.

Embodiment 1: An apparatus for stabilizing a limb against flexion around a joint of the limb, comprising: a joint member having an intermediate portion disposed between a first end portion and a second end portion of the joint member; a first movable member removably attachable to the first end portion; and a second movable member removably attachable to the second end portion; wherein the intermediate portion is configured to receive the joint; and wherein the second end portion is angled from the first end portion at a joint angle that is opposite to a flexion direction of the limb about the joint.

Embodiment 2: The apparatus of Embodiment 1, wherein the first movable member, when attached to the first end portion, and the second movable member, when attached to the second end portion, form an aperture at the joint.

Embodiment 3: The apparatus of Embodiment 2, wherein the joint is an elbow and the AC fossa of the limb, which is an arm, is visible through the aperture when the first movable member is attached to the first end portion and the second movable member is attached to the second end portion.

Embodiment 4: The apparatus of Embodiment 2, wherein the aperture is formed by a first tapered portion of the first movable member and a second tapered portion of the second movable member.

Embodiment 5: The apparatus of Embodiment 1, wherein the joint angle is between 30 degrees and 60 degrees.

Embodiment 6: The apparatus of Embodiment 1, wherein when the limb is received in the joint member, the intermediate portion is a first point of contact against the joint, the first movable member is a second point of contact against a first portion of the limb spaced a first direction from the joint, and the second movable member is a third point of contact against a second portion of the limb spaced a second direction from the joint that is opposite to the first direction.

Embodiment 7: The apparatus of Embodiment 1, further comprising padding that is attachable to interior surfaces, which face the limb when the limb is received in the apparatus, of the joint member, the first movable member, and the second movable member.

Embodiment 8: The apparatus of Embodiment 1, further comprising a flexible anti-pinching layer that is attached to at least some edges of the joint member, the first movable member, and the second movable member that contact each other when the first movable member is attached to the first end portion and the second movable member is attached to the second end portion.

Embodiment 9: The apparatus of Embodiment 1, wherein the joint member, the first movable member, and the second movable member are cut from a structural pipe fitting.

Embodiment 10: The apparatus of Embodiment 1, wherein the first movable member is attached to the first end portion and the second movable member is attached to the second end portion based on a clamshell attachment.

Embodiment 11: A method, comprising: receiving a joint of a limb in an intermediate portion of a joint member, the intermediate portion disposed between a first end portion and a second end portion of the joint member, and the second end portion being angled from the first end portion at a joint angle; positioning the joint member so that the joint angle is opposite to a flexion direction of the limb about the joint; removably attaching a first movable member, which has a first tapered portion, to the first end portion; removably attaching a second movable member, which has a second tapered portion, to the second end portion; and forming an aperture at the joint with the first tapered portion and the second tapered portion so that the joint is visible through the aperture.

Embodiment 12: The method of Embodiment 11, further comprising disposing an intravenous device in the limb at the aperture and performing peripheral intravenous cannulation using the intravenous device when the first and second movable members are removably attached to the joint member.

Embodiment 13: The method of Embodiment 11, further comprising disposing an intravenous device in the limb, which is an arm, at the aperture and performing peripheral intravenous cannulation of the AC fossa using the intravenous device when the first and second movable members are removably attached to the joint member.

Embodiment 14: The method of Embodiment 11, further comprising preventing flexion of the limb, which is an arm, about the joint, which is an elbow, based on applying a first point of contact against the elbow using the intermediate portion, a second point of contact against a bicep or a forearm of the arm using the first movable member, and a third point of contact against the other of the bicep and the forearm using the second movable member.

Embodiment 15: An apparatus for stabilizing an arm against flexion around an elbow of the arm, comprising: a joint member having an intermediate portion disposed between a first end portion and a second end portion of the joint member; a first movable member removably attachable to the first end portion, the first movable member having a first tapered portion; and a second movable member removably attachable to the second end portion, the second movable member having a second tapered portion; wherein the intermediate portion is configured to receive the elbow; wherein the second end portion is angled from the first end portion at a joint angle that is opposite to a flexion direction of the arm about the elbow; and wherein the first tapered portion and the second tapered portion form an aperture when the first movable member is attached to the first end portion and the second movable member is attached to the second end portion.

Embodiment 16: The apparatus of Embodiment 15, further comprising foam or gel padding that is removably attachable to interior surfaces, which face the arm when the arm is received in the apparatus, of the joint member, the first movable member, and the second movable member.

Embodiment 17: The apparatus of Embodiment 15, further comprising a silicone layer that is attached to edges of the joint member, the first movable member, and the second movable member that contact each other when the first movable member is attached to the first end portion and the second movable member is attached to the second end portion.

Embodiment 18: The apparatus of Embodiment 15, wherein the joint member, the first movable member, and the second movable member are cut from a same PVC or ABS elbow pipe fitting.

Embodiment 19: The apparatus of Embodiment 15, wherein the joint member, the first movable member, and the second movable member are cut from a same 4" diameter, 5" diameter, or 6" diameter elbow pipe fitting.

Embodiment 20: The apparatus of Embodiment 15, further comprising a plurality of ladder, bail, and lever systems that removably attach the first movable member to the first end portion and the second movable member to the second end portion.

In at least some exemplary embodiments, the exemplary disclosed system, apparatus, and method may provide an efficient and effective system for maintaining and/or assisting in establishing effective peripheral intravenous access (PIV) in the AC fossa. For example, the exemplary disclosed system, apparatus, and method may provide an efficient and effective system for comfortably stabilizing a patient's arm to substantially prevent flexion at the elbow or knee (e.g., or other joint), thereby substantially preventing negative effects from the routine displacement and resulting transient occlusion and/or infiltration that often render a PIV in the AC fossa non-functional. The exemplary disclosed system, apparatus, and method may provide an effective (e.g., and comfortable) technique for maintaining a patient's arm or leg (e.g., or other hinged joint) in an extended position and to substantially prevent flexion about the elbow or knee.

It will be apparent to those skilled in the art that various modifications and variations can be made to the exemplary disclosed system, apparatus, and method. Other embodiments will be apparent to those skilled in the art from consideration of the specification and practice of the exemplary disclosed apparatus, system, and method. It is intended that the specification and examples be considered as exemplary, with a true scope being indicated by the following claims.

What is claimed is:

1. An apparatus for stabilizing configured to stabilize a limb against flexion around a joint of the limb, comprising:

a joint member having an intermediate portion disposed between a first end portion and a second end portion of the joint member;

a first movable member removably attachable to the first end portion; and a second movable member removably attachable to the second end portion;

wherein the intermediate portion is configured to receive the joint;

wherein the second end portion is angled from the first end portion at a joint angle that is configured to be opposite to a flexion direction of the limb about the joint; and wherein a surface of the intermediate portion configured to face the joint is convex toward the joint.

2. The apparatus of claim 1, wherein the first movable member, when attached to the first end portion, and the second movable member, when attached to the second end portion, form an aperture at the joint.

3. The apparatus of claim 2, wherein the joint is an elbow and the antecubital fossa of the limb, which is an arm, is visible through the aperture when the first movable member is attached to the first end portion and the second movable member is attached to the second end portion.

4. The apparatus of claim 2, wherein the aperture is formed by a first tapered portion of the first movable member and a second tapered portion of the second movable member.

5. The apparatus of claim 1, wherein the joint angle is between 30 degrees and 60 degrees.

6. The apparatus of claim 1, wherein when the limb is received in the joint member, the intermediate portion is a first point of contact against the joint, the first movable member is a second point of contact against a first portion of the limb spaced a first direction from the joint, and the second movable member is a third point of contact against a second portion of the limb spaced a second direction from the joint that is opposite to the first direction.

7. The apparatus of claim 1, further comprising padding that is attachable to interior surfaces, which face the limb when the limb is received in the apparatus, of the joint member, the first movable member, and the second movable member.

8. The apparatus of claim 1, further comprising a flexible anti-pinching layer that is attached to at least some edges of the joint member, the first movable member, and the second movable member that contact each other when the first movable member is attached to the first end portion and the second movable member is attached to the second end portion.

9. The apparatus of claim 1, wherein the joint member, the first movable member, and the second movable member are cut from a structural pipe fitting.

10. The apparatus of claim 1, wherein the first movable member is attached to the first end portion and the second movable member is attached to the second end portion based on a clamshell attachment.

11. An apparatus configured to stabilize an arm against flexion around an elbow of the arm, comprising:

a joint member having an intermediate portion disposed between a first end portion and a second end portion of the joint member;

a first movable member removably attachable to the first end portion, the first movable member having a first tapered portion; and a second movable member removably attachable to the second end portion, the second movable member having a second tapered portion;

wherein the intermediate portion is configured to receive the elbow;

wherein the second end portion is angled from the first end portion at a joint angle that is configured to be opposite to a flexion direction of the arm about the elbow;

wherein the first tapered portion and the second tapered portion form an aperture when the first movable member is attached to the first end portion and the second movable member is attached to the second end portion; and wherein a surface of the intermediate portion configured to face the joint is concave outward toward the joint.

12. The apparatus of claim 11, further comprising foam or gel padding that is removably attachable to interior surfaces, which face the arm when the arm is received in the apparatus, of the joint member, the first movable member, and the second movable member.

13. The apparatus of claim 11, further comprising a silicone layer that is attached to edges of the joint member, the first movable member, and the second movable member that contact each other when the first movable member is attached to the first end portion and the second movable member is attached to the second end portion.

14. The apparatus of claim 11, wherein the joint member, the first movable member, and the second movable member are cut from a same polyvinyl chloride or acrylonitrile butadiene styrene elbow pipe fitting.

15. The apparatus of claim 11, wherein the joint member, the first movable member, and the second movable member are cut from a same 4" diameter, 5" diameter, or 6" diameter elbow pipe fitting.

16. The apparatus of claim 11, further comprising a plurality of ladder, bail, and lever systems that removably attach the first movable member to the first end portion and the second movable member to the second end portion.

17. A method, comprising:

configuring an intermediate portion of a joint member to receive a joint of a limb, the intermediate portion disposed between a first end portion and a second end portion of the joint member, and the second end portion being angled from the first end portion at a joint angle;

positioning the joint member so that the joint angle is configured to be opposite to a flexion direction of the limb about the joint;

removably attaching a first movable member, which has a first tapered portion, to the first end portion;

removably attaching a second movable member, which has a second tapered portion, to the second end portion; and forming an aperture at the joint with the first tapered portion and the second tapered portion so that the joint is visible through the aperture;

wherein a surface of the intermediate portion configured to face the joint is convex toward the joint.

18. The method of claim 17, further comprising disposing an intravenous device in the limb at the aperture and performing peripheral intravenous cannulation using the intravenous device when the first and second movable members are removably attached to the joint member.

19. The method of claim 17, further comprising disposing an intravenous device in the limb, which is an arm, at the aperture and performing peripheral intravenous cannulation of the antecubital fossa using the intravenous device when the first and second movable members are removably attached to the joint member.

20. The method of claim 17, wherein the joint member is configured to prevent flexion of the limb, which is an arm, about the joint, which is an elbow, based on applying a first point of contact against the elbow using the intermediate portion, a second point of contact against a bicep or a forearm of the arm using the first movable member, and a third point of contact against the other of the bicep and the forearm using the second movable member.

* * * * *